(12) United States Patent
Ostermeier et al.

(10) Patent No.: US 8,685,637 B2
(45) Date of Patent: Apr. 1, 2014

(54) KIT FOR SPERM CRYOPROTECTION

(71) Applicant: The Jackson Laboratory, Bar Harbor, ME (US)

(72) Inventors: G. Charles Ostermeier, Frederick, MD (US); Jane S. Farley, Ellsworth, ME (US); Robert Taft, Southwest Harbor, ME (US); Michael V. Wiles, Mount Desert, ME (US)

(73) Assignee: The Jackson Laboratory, Bar Harbor, ME (US)

( * ) Notice: Subject to any disclaimer, the term of this patent is extended or adjusted under 35 U.S.C. 154(b) by 0 days.

(21) Appl. No.: 13/723,721

(22) Filed: Dec. 21, 2012

(65) Prior Publication Data

US 2013/0122483 A1 May 16, 2013

Related U.S. Application Data

(60) Continuation of application No. 13/165,265, filed on Jun. 21, 2011, now Pat. No. 8,420,307, which is a division of application No. 11/811,968, filed on Jun. 12, 2007, now Pat. No. 8,435,729.

(60) Provisional application No. 60/812,833, filed on Jun. 12, 2006, provisional application No. 60/840,744, filed on Aug. 29, 2006, provisional application No. 60/854,501, filed on Oct. 25, 2006.

(51) Int. Cl.
*A01N 1/02* (2006.01)

(52) U.S. Cl.
USPC .............................. 435/2; 435/307.1; 604/319

(58) Field of Classification Search
USPC ........................................................ 435/2
See application file for complete search history.

(56) References Cited

U.S. PATENT DOCUMENTS

| | | | |
|---|---|---|---|
| 4,007,087 A * | 2/1977 | Ericsson ......................... | 435/2 |
| 6,194,136 B1 * | 2/2001 | Livesey et al. .................. | 435/1.3 |
| 6,368,786 B1 | 4/2002 | Saint-Ramon et al. | |
| 2002/0159984 A1 | 10/2002 | Brown | |
| 2003/0186212 A1 | 10/2003 | Loskutoff et al. | |
| 2003/0215782 A1 | 11/2003 | Kusakabe et al. | |
| 2004/0121303 A1* | 6/2004 | Gavin et al. ....................... | 435/2 |
| 2006/0210697 A1* | 9/2006 | Mower ........................... | 426/658 |
| 2008/0200548 A1 | 8/2008 | Goldstein | |

FOREIGN PATENT DOCUMENTS

| | | |
|---|---|---|
| EP | 0435911 A1 | 7/1991 |
| EP | 1051907 A1 | 11/2000 |
| JP | 20052058 A | 8/2006 |
| WO | WO-9714785 A2 | 4/1997 |
| WO | WO-9800125 A1 | 1/1998 |
| WO | WO-02054864 A1 | 7/2002 |
| WO | WO-2006051200 A1 | 5/2006 |

OTHER PUBLICATIONS

Berlinguer, F. et al., Superoxide dismutase affects the viability of thawed European mouflon (*Ovis g. musimon*) semen and the heterologous fertilization using both IVF and intracytoplasmatic sperm injection, *Reproduction, Fertility and Development*, 15: 19-25, 2003.

Bilodeau, J. et al., Levels of Antioxidant Defenses are Decreased in Bovine Spermatozoa After a Cycle of Freezing and Thawing, *Molecular Reproduction and Development*, 55(3):282-88, 2000.

Dalvit, G. et al., Effect of alpha-tocopherol and ascorbic acid on bovine in vitro fertilization, *Theriogenology*. 49(3):619-27, 1998.

Marco-Jimenez, F, et al., Cryopreservation of Rabbit Spermatozoa with Freezing Media Supplemented with Reduced and Oxidised Glutathione, *Cryo Letters*, 27(4):261-8, 2006.

Sánchez-Partida, L. et al., Epididymal compounds and antioxidants in diluents for the frozen storage of ram spermatozoa, *Reproduction, Fertility and Development*, 9(7):689-96, 1997.

Wiles, M. et al., The Sophisticated Mouse: Protecting a Precious Reagent, *Methods in Molecular Biology*, 602:23-36, 2010.

Watson, P., The causes of reduced fertility with cryopreserved semen, *Animal Reproduction Science*, 60-61: 481-92, 2000.

(Author unknown), Mouse Sperm Cryopreservation, *National Institute of Child Health and Human Development*, Oct. 1998.

Mazur, P. et al., Cryopreservation of the Germplasm of Animals Used in Biological and Medical Research: Importance, Impact, Status, and Future Directions, *Biology of Reproduction*, 78: 2-12, 2008.

Katkov, I. et al., Mouse Spermatozoa in High Concentrations of Glycerol: Chemical Toxicity vs osmotic Shock at Normal and Reduced Oxygen Concentrations, Cryobiology, 37: 325-38, 1998.

Koshimoto, C. et al., Effect of Osmolality and Oxygen Tension on the Survival of Mouse Sperm Frozen to Various Temperatures in Varoius Concentrations of Glycerol and Raffinose, Cryobiology, 41: 204-31, 2000.

Malakoff, D., The Rise of the Mouse, Biomedicine's Model Mammal, Science, 288(5464): 248-53, Apr. 2000.

Liu, L. et al., Sperm Freezing and in Vitro Fertilization in Three Substrains of C57BL/6 Mice, Journal of the American Association for Laboratory Animal Science, 48(1): 39-43, Jan. 2009.

Mombaerts, P., JAX® Sperm Cryopreservation, A Customer's Perspective, The Jackson Laboratory, pp. 1-5, Dec. 2007.

Luberda, Z. The role of glutathione in mammalian gametes. *Reproductive Biology*, 5(1): 5-17, 2005.

Tada, N. et al., (1993). Effect of pre-freezing equilibration and post-thawing centrifugation on the fertilizing capacity of frozen mouse epididymal spermatozoa. Cryo Lett 14, 195-206.

(Continued)

*Primary Examiner* — Michael G Wityshyn
*Assistant Examiner* — Tiffany Gough
(74) *Attorney, Agent, or Firm* — Gifford, Krass, Sprinkle, Anderson & Citkowski, P.C.

(57) ABSTRACT

Described herein are kits for use in cryopreserving mammalian sperm including a composition that comprises a cryoprotectant; a membrane protectant that stabilizes or assists in stabilization of membranes of sperm; and monothioglycerol.

17 Claims, 11 Drawing Sheets

(56) References Cited

OTHER PUBLICATIONS

Takeo, T. et al., Combination medium of cryoprotective agents containing L-glutamine and methyl-b-cyclodextrin in a preincubation medium yields a high fertilization rate for cyropreserved C57BL/6J mouse sperm. Laboratory Animals, 44: 132-137, 2010.
Agca et al., "Osmotic Characteristics of Mouse Spermatozoa in the Presence of Extenders and Sugars," *Biology of Reproduction* 67: 1493-1501 (2002).
Atmaca "Antioxidant Effects of Sulfur-Containing Amino Acids," *Younsei Medical Journal* 45(5): 776-788 (2004).
Bath "Simple and Efficient in Vitro Fertilization with Cryopreserved C57BL/6J," *Biology of Reproduction* 68:19-23 (2003).
Byers et al., Performance of Ten Inbred Mouse Strains Following Assisted Reproductive Technologies (ARTS) *Elsevier* 65:1716-1726 (2006).
Gilmore et al., "Effects of Cryopretectant Solutes on Water Permeability of Human Spermatozoa," *Biology of Reproduction* 53:985-995 (1995).
Glenister et al., "Cryoconservation Archiving for the Future," *Mammalian Genome* 11:565-51 (2000).
Graaf et al., "The Influence of Antioxidant, Cholesterol and Seminal Plasma on the in Vitro Quality of Sorted and Non-Sorted ram Spermatozoa," *Theriogenology* 37:217-227 (2007).
Gunstone et al., "Lipid Glossary 2," *The Oil Press* Mar. 2000.
Guthrie et al., "Determination of Intracellular Reactive Oxygen Species and High Mitochondrial Membrane Potential in Percoll-Treated Viable Boar Sperm Using Fluorescence-Activated Flow Cytometry," *J. Anim. Sci* 84:2089-2100 (2006).
Kusakabe et al., "Maintenance of Genetic Integrity in Frozen and Freeze-Dried Mouse Spermatozoa," *PNAS* 98(24): 13501-13506 (2001).
Nakagata "Cryopreservation of Mouse Spermatozoa," *Mammalian Genome*. 11:572-576 (2000).
Nakagata "Mouse Spermatozoa Cryopreservation," *J. Mamm. Ova Res.* 17: 1-8 (2000).
Nakagata et al., "Cryopreservation of Mouse Spermatozoa from Inbred and F1 Hybrid Strains," *Exp. Anim.* 42(3):317-320 (1993).
Neild et al., "Lipid Peroxide Formation in Relation to Membrane Stability of Fresh and Frozen Thawed Stallion Spermatozoa," *Molecular Reproduction and Development* 72:230-238 (2005).
Nishizono et al., "Decrease of Fertilizing Ability of Mouse Spermatozoa After Freezing and Thawing is Related to Cellular Injury," *Biology of Reproduction* 71:973-978 (2004).
Penfold et al., "A New Method for Cryopreservation of Mouse Spermatozoa," *Journal of Reproduction and Fertility* 99:131-134 (1993).
Nakagata, N. et al., Positive Effect of Partial Zona-Pellucida Dissection on the In Vitro Fertilizing Capacity of Cryopreserved C57BL/6J Transgenic Mouse Spermatozoa of Low Motility, *Biology of Reproduction*, 57: 1050-55, 1997.
Phelps et al., "Effects of percol separation, cryoprotective agents, and temperature on plasma membrane permeability characteristics of murine spermatozoa and their relevance to cryopreservation," *Biology of Reproduction* 61:1031-1041, 1999.
Quinn, "Enhanced results in mouse and human embryo culture using a modified human tubal fluid medium lacking glucose and phosphate," *Journal of Assisted Reproduction and Genetics* 12(2): 97-105 (1995).
Seburn et al., "Reliable new sperm cryopreservation service developed at the Jackson Laboratory," *JAX Notes* No. 504, Winter 2006.
Songsasen et al., "Birth of live mice resulting from oocytes fertilized in vitro with cryopreserved spermatozoz," *Biology of Reproduction* 56:143-152, 1997.
Songsasen et al., "Cryopreservation of mouse spermatozoa," *Cryobiology* 35:240-254, 1997.
Songsasen et al., "Cryopreservation of mouse spermatozoa," Cryobiology 35:255-269, 1997.
Spector et al., "Chemically defined lipid concetrate," Gibco Invitrogen Corporation, Form No. 3115 Jun. 2001.
Stacey et al., "Thermal characterization of Nakagata's mouse sperm freezing protocol," Cryobiology 52:99-107 (2006).
Suquet et al., "Cryopreservation of sperm in marine fish," Aquaculture Research 31(3):231-243, 2000.
Szczygiel et al., "Intracytoplasmic sperm injection is more efficient than in vitro fertilization for generating mouse embryos from cryopreserved spermatozoa," *Biology of Reproduction* 67:1278-1284, 2002.
Sztein et al., "Comparison of permeating and nonpermeating cryoprotectants for mouse sperm cryopreservation," *Cryobiology* 41:28-39, 2001.
Sztein et al., "In vitro fertilization with cryopreserved inbred mouse sperm," *Biology of Reproduction* 63:1774-1780, 2000.
Thorton et al., "Large numbers of mice established by in vitro fertilization with cryopreserved spermatozoa: implications and application for genetic resource banks, mutagenesis screens, and mouse backcrossed," *Mammalisn Genome* 10:987-992, 1999.
Walters et al., "Osmotic tolerance of mouse speratozoa from various genetic backgrounds: acrosome integrity, membrane integrity, and maintenance of motility," *Cryobiology* 50:193-205, 2005.
Ward et al., "Long-term preservation of mouse spermatozoa after freeze-drying and freezing withou cryoprotection," *Biology of Reproduction* 69:2100-2108, 2003.
Yamauchi et al., "Preservation of ejaculated mouse spermatozoa from fertile C57BL/6 and infertile Hook1/Hook1 mouse collected from the uteri of mated females," Biology of Reproduction 76:1002-1008, 2007.
Yildiz et al., "Effects of cryopreservation on sperm quality, nuclear DNA integrity, in vitro fertilization, and in vitro embryo development in the mouse," Reproduction Research 133:585-595, 2007.
No author provided, "Embryo Aggregation," University of Wisconsin Biotechnology Center, printed from web Jun. 22, 2007.
No author provided "A dramatic breakthrough in colony management," The Jackson Laboratory, printed from web Apr. 16, 2007.
Agnihotri et al., "Regional heterogeneity in intracellular distribution of superoxide and hydrogen peroxide and its relation to sperm development," Archives of Andrology 43:113-121, 1999 (Abstract only).
Baumber et al., "Assessment of the cryopreservation of equine speratozoa in the presence of enzyme scavengers and antioxidants," American Journal of Veterinary Research 66:772-779, 2005 (abstract only).
Bilodeau et al., "Thiols prevent H2O2 mediated loss of sperm motility in cryopreserved bull semen," *Theriogenolgy* 56:275-286, 2001.
Bugrov et al., "Role of some cryprotectants in the freezing of semen," *Kriobiologyia i kriomeditsina* 6:5-9, 1980 (abstract only).
Foote et al., "Fertility of bull semen frozen with beta amylase, beta-glucoronidase, and catalase" *Journal of Dairy Science* 59:2014-2017, 1976 (abstract only).
Foote et al., "Motility and fertility of bull sperm in whole milk extender containing antioxidants" *Animal Reproduction Science* 71:13-23, 2002 (abstract only).
Gardon et al., "Addition of reduced glutothionine to thawing medium improved the sperm motility and reduced ros generation in frozen ovine and caprine spermatozoa," Reproduction Fertility and Development 18:1-2, 2006 (abstract only).
Kumar et al., "Effect of additives and their combinations on storageability and freezability of bovine semen in milk diluents," Indian Vet. Med. Journal 20:113, 1996.
Lindemann et al., "An investigation of the effectiveness of certain antioxidants in preserving motility of reactivated bull sperm models," 38:114-120, 1988.
Mahadevan et al., "Effect of cryoprotective media and dilution methods on the preservation of human spermatozoa," Andrologia 15:355-366, 1983 (abstract only).
Matas et al., "The effect of different treatments of porcine ejaculated and epididymal spermatozoa on ROS generation," Reproduction Fertility and Development 18:1-2, 2006 (abstract only).
Ostermeier et al., "Conserving distributing and managing genetically modified mouse lines by sperm cryopreservation," Plos One 3(7): E2792, 2008.
Rao et al., "Improved recovery of post-thaw motility and vitality of human spermatozoa cryopreserved in the presence of dithiothreitol," Cryobiology 21:536-541, 1984.

(56) References Cited

OTHER PUBLICATIONS

Renard et al., "Evaluation of extenders for pejerrey odonthestes bonariensis sperm," Fisheries Science 60:661-666, 1994 (abstract only).

Roca et al., "Survival and fertility of boar spermatozoa aftter freeze-thawing in extended supplemented with butylated hydroxybutylene," Journal of Andrology 25:397-405, 2004 (abstract only).

Schmidt et al., "Freezing of boar semen," Archive fuer Tierzucht 17:85-94, 1974 (abstract only).

Singh et al., "Comparison of cysteine fortified citric acid whey with tris and egg yolk citrate extenders on cryopreservation of buffalo semen," *Indian Journal of Dairy Science* 49(1): 24-28, 1996.

Snedeker et al., "Dimethyl sulfoxide as a cryoprotective agent for freezing bovine semen," *Journal of Animal Science* 30:953-956, 1970 (abstract only).

Stoss et al. "Short-term and cryopreservation of rainbow trout sperm," *Annales de Biologie Animate, biochimie, biophysique* 18:1077-1082, 1978 (abstract only).

Takeo, T. et al., Mouse Sperm Cryopreservation and Effective Embryo Production Using Cryopreserved C57BL/6 Mourse Sperm, *J. Mamm. Ova Res*, 27:70-78, 2010.

Sperm Cryopreservation Protocol, The Jackson Laboratory, first distributed Nov. 5, 2007.

JAX® Sperm Cryopreservation Kit Manual, The Jackson Laboratory, Feb. 2009.

JAX® Sperm Cryopreservation Kit Manual, The Jackson Laboratory, Sep. 2010.

Dong, Q. et al., Antioxidants, Oxyrase, and mitochondrial uncoupler 2,4-dinitrophenol improved postthaw survival of rhesus monkey sperm from ejaculates with low cryosurvival, *Fertility and Sterility*, 94(6): 2359-2361, Nov. 2010.

Katkov, I., Mouse Spermatozoa in High Concentrations of Glycerol: Chemical Toxicity vs Osmotic Shock at Normal and Reduced Oxygen Concentrations, *Cryobiology*, 37(4): 325-338, 1998.

Koshimoto, C., Effect of osmolality and oxygen tension on the survival of mouse sperm frozen to various temperatures in various concentrations of glycerol and raffinose, *Cryobiology*, 41(3): 204-231, 2000.

Koshimoto, C., Effects of cooling and warming rate to and from −70° C, and effect of further cooling from −70 to −196° C on the motility of mouse spermatozoa, *Biology of Reproduction*, 66(5):1477-1484, 2002.

Mazur, P, The enhancement of the ability of mouse sperm to survive freezing and thawing by the use of high concentrations of glycerol and the presence of an *Escherichia coli* membrane preparation (oxyrase) to lower the oxygen concentration, *Cryobiology*, 40: 187-209, 2000.

Takahashi, H. et al., Archiving and Distributing Mouse Lines by Sperm Cryopreservation, IVF, and Embryo Transfer, *Methods in Enzymology*, 476: 53-69, 2010.

Bailey, J.L. et al. Semen Cryopreservation in Domestic Animals: A Damaging and Capacitating Phenomenon. Journal of Andrology, 21(1):1-7, 2000.

* cited by examiner

Legend for x axis: Concentration of MTG Treatment

Legend for y axis: % Oocytes Developing to 2-Cell embryos

FIGURE 1: Monothioglycerol enhances the fertility of cryopreserved C57BL/6J sperm Legend for x axis: Concentration of GSH Treatment;

Legend for y axis: % Oocytes Developing to 2-Cell Embryos

FIGURE 2: GSH enhances the fertility of cryopreserved C57BL/6J sperm

In this figure C57BL/6J is abbreviated with B6 and BALB/cByJ with BALB/cby.

% embryos transferred developing to term

% embryos transferred developing to term

KIT FOR SPERM CRYOPROTECTION

REFERENCE TO RELATED APPLICATIONS

This application is a continuation of U.S. patent application Ser. No. 13/165,265, filed Jun. 21, 2011, which is a divisional of U.S. patent application Ser. No. 11/811,968, filed Jun. 12, 2007, which claims priority to U.S. Provisional Application Nos. 60/812,833, filed Jun. 12, 2006; 60/840,744, filed Aug. 29, 2006; and 60/854,501, filed Oct. 25, 2006. The entire content of all of which is incorporated herein by reference in their entirety.

STATEMENT REGARDING FEDERALLY SPONSORED RESEARCH

This invention was made with government support under Grant No. RR01262-24, awarded by the National Institutes of Health. The government has certain rights in the invention.

BACKGROUND OF THE INVENTION

Revolutionary advances in genome research and the ability to create genetically specific strains of mice have resulted in an exponential increase in the number of mouse strains available for biomedical research. These newly created strains, particularly those in which the strain or mutation can be maintained by haploid germplasm, are most efficiently preserved by freezing and storing sperm. The methods currently employed for cryopreservation of mouse sperm display variably moderate success, are dependent on the genetic constitution of the male and have, thus, in general, been deemed inadequate for the safe preservation of most inbred mouse strains. Additional methods for cryopreservation of sperm, which are less adversely affected by genetic background, are needed.

SUMMARY OF THE INVENTION

The cryoprotective media and methods of the present invention, which include methods of cryogenically preserving sperm (e.g., mammalian, including human and non human mammals, such as rodent, including mouse and rat, sperm) are of great interest because they consistently increase the success rates obtained with cryopreserved sperm. As used herein, the term sperm refers to sperm and spermatozoa. The cryopreservation media (also referred to as cryoprotective media) of the invention comprises, in one embodiment, a cryoprotectant (also referred to as a cryoprotective agent); a membrane protectant that stabilizes or assists in stabilization of membranes of sperm; and a free radical scavenger (e.g., a reducing agent, an antioxidant). This cryoprotection media is referred to herein as CPM.

In an alternative embodiment, the cryopreservation media includes two of the above-listed components: a cryoprotectant (CP) and a free radical scavenger (FRS). This cryopreservation media is referred to as CP-FRS.

In a further embodiment, the cryoprotection media includes a free radical scavenger. This cryoprotection media is referred to as FRS.

As used herein, the term "a" includes or refers to "at least one" and also "one or more." In all embodiments, additional substances (e.g., a solvent or liquid, such as water or a physiological buffer; anti-bacterial agent(s); antibiotic(s); antiviral agent(s)) can be included, as needed.

In particular embodiments, such as those in which rodent (e.g., mouse, rat), bovine or human sperm are cryopreserved, the cryopreservation media (CPM) used comprises a (at least one; one or more) cryoprotectant, such as a sugar; a (at least one; one or more) membrane protectant; and a free radical scavenger (at least one; one or more), such as a reducing agent, such as monothioglycerol (MTG) and/or an antioxidant, such as reduced glutathione (GSH). In specific embodiments, the sugar is a trisaccharide, such as raffinose, or a disaccharide, such as lactose. In additional embodiments, the cryoprotectant is glycerol or propylene glycol, which can be used alone or in combination with each other (glycerol/propylene glycol together) or in combination with raffinose and/or lactose (e.g., raffinose and/or lactose in combination with glycerol and/or propylene glycol). In specific embodiments, the membrane protectant is a protein, a non-protein or a combination of a protein and a non-protein. In specific embodiments, the membrane protectant is milk, skim milk, egg yolk or a component of/in/derived from any of the foregoing.

DETAILED DESCRIPTION OF THE INVENTION

Figure 1:
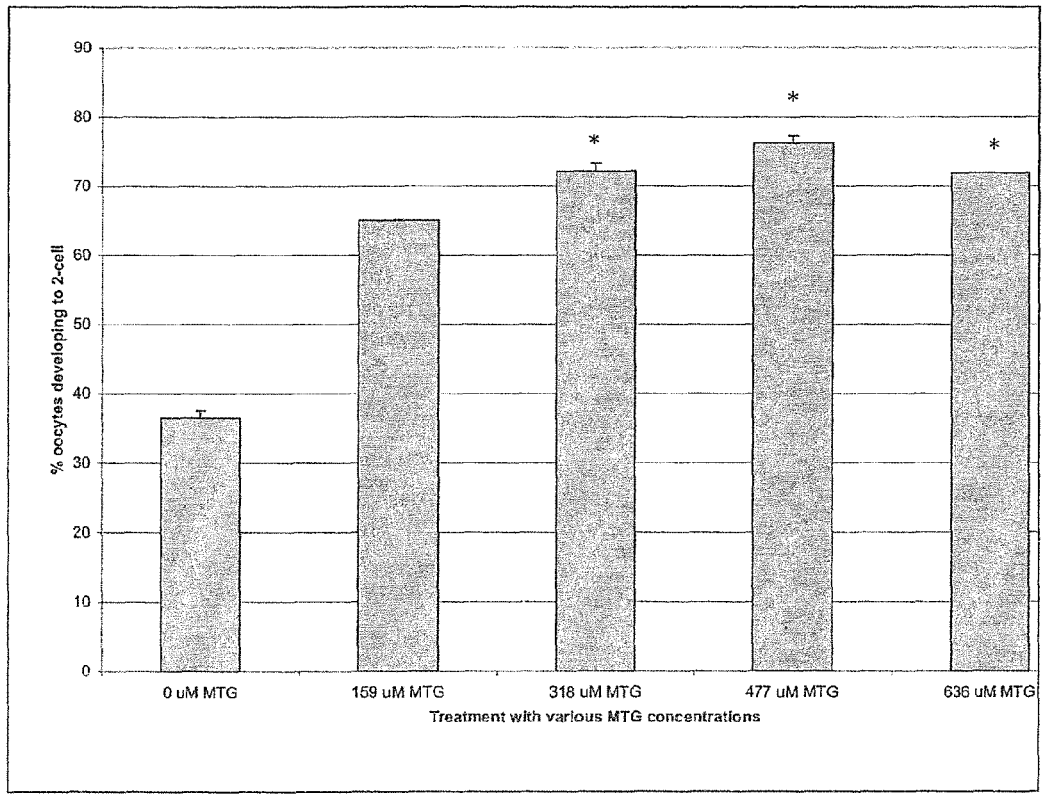
FIG. 1 shows that monothioglycerol enhances the fertility of cryopreserved C57BL/6J sperm.

Described herein is a composition, referred to as cryoprotective media or cryoprotection media, useful for cryopreservation of sperm from a wide variety of mammals and non-mammals. In one embodiment, the cryoprotective media is referred to as CPM and comprises a cryoprotectant; a membrane protectant that stabilizes or assists in stabilization of membranes of sperm; and a free radical scavenger (e.g., a reducing agent, an antioxidant). As used herein, with reference to CPM, CP-FRS and FRS (all types of cryoprotective media described herein), the term "free radical scavenger" refers to a substance or agent that removes or inactivates free radicals, such as a substance or agent added to a mixture in order to remove or inactivate free radicals. As used herein, with reference to CPM, CP-FRS and FRS (all types of cryoprotective media described herein), the term "reducing agent" refers to an element or a compound which, in a redox (reduction-oxidation) reaction, reduces another species (element or compound). As used herein, with reference to CPM, CP-FRS and FRS (all types of cryoprotective media described herein), the term "antioxidant" refers to a substance or agent that reduces oxidative damage to cells and biomolecules. The composition typically additionally comprises water in sufficient quantity to maintain functionality of sperm. Alternatively, a liquid or solvent other than water, such as saline, or a physiological buffer, such as phosphate (PBS), bicarbonate, HEPES, MOPS, CHES, MES, CAPS or Tris, can be used, alone or in combination with water.

In another embodiment, the cryoprotective media includes a cryoprotectant and a free radical scavenger and does not include a membrane protectant. The cryoprotective media, referred to herein as CP-FRS, is useful for cryopreservation of sperm from a wide variety of mammals and non-mammals. In a further embodiment, the cryoprotective media includes a free radical scavenger and does not include a cryoprotectant or a membrane protectant. In these embodiments, the composition typically additionally comprises water in sufficient quantity to maintain functionality of sperm, as well as additional components, as described herein.

The composition can be used for cryopreservation of sperm, including mammalian sperm, such as rodent (e.g., mouse, rat), bovine, canine, feline, swine, goat, sheep, rabbit, horse, camelida, pet or companion mammal and human sperm, as well as non-mammalian sperm, such as avian (e.g., chicken, turkey, pet or companion bird) and fish (those produced for consumption, pet or companion fish) sperm. The cryoprotective media is useful for cryopreservation of sperm obtained from vertebrates of all types, such as mammals, including genetically modified vertebrates of all types, including genetically modified mammals (e.g., sperm obtained from genetically modified rodent (e.g., mouse, rat), bovine, canine, feline, swine, goat, sheep, rabbit, horse, camelida, other pet or companion mammal), as well as genetically modified non-mammals (such as sperm obtained from genetically modified birds (e.g., chicken, turkey, companion bird) and fish (those produced for consumption, companion fish)). The composition described herein can be used in any method for cryogenically preserving sperm.

In one embodiment, the method of cryogenically preserving sperm (producing cryogenically preserved sperm) comprises (a) combining sperm to be cryogenically preserved and a composition that comprises at least one of the following: (1) a cryoprotectant; (2) a membrane protectant that stabilizes or assists in stabilization of membranes of sperm; and (3) a free radical scavenger (such as a reducing agent or an antioxidant), to produce a combination (cryoprotective media-sperm combination, also referred to as the initial combination or the combination to be cryopreserved) and (b) subjecting the combination to conditions that result in cryopreservation of sperm in the combination, thereby producing a cryogenically preserved combination that comprises cryogenically preserved sperm.

In a specific embodiment, the method of cryogenically preserving sperm (producing cryogenically preserved sperm) comprises (a) combining sperm to be cryogenically preserved and a composition, referred to as CPM, that comprises: (1) a cryoprotectant; (2) a membrane protectant that stabilizes or assists in stabilization of membranes of sperm; and (3) a free radical scavenger (such as a reducing agent or an antioxidant), to produce a combination (cryoprotective media-sperm combination, also referred to as the initial combination or the combination to be cryopreserved) and (b) subjecting the combination to conditions that result in cryopreservation of sperm in the combination, thereby producing a cryogenically preserved combination that comprises cryogenically preserved sperm.

The initial combination (the combination to be cryopreserved) is produced prior to cryopreservation and can be subjected to conditions that result in cryopreservation of sperm in the combination immediately after production or within a limited period after it is produced. Cryopreservation can be carried out at any time after production that does not adversely affect the viability of the sperm, such as, for mouse sperm, any time within about 90 minutes after it is produced. The resulting sperm are cryopreserved sperm that exhibit consistently better fertilization potential than the fertilization potential of cryopreserved sperm obtained using presently available methods and media. Preservation can be carried out at a temperature of from about plus 4° C. to about minus 200° C. In specific embodiments, cryopreservation is carried out at a temperature between from about minus 80° C. to about minus 200° C. In all embodiments described herein, the resulting cryopreserved sperm can be stored indefinitely at an appropriate temperature, known to those of skill in the art (e.g., at temperatures that range from about minus 80° C. to about minus 200° C.).

The fertilization capacity or ability of sperm can be assessed using methods known to those of skill in the art, such as by an in vitro method (e.g., by assessing the ability to fertilize oocytes with which they are combined/incubated (their ability to form 2-cell embryos, for example)) and/or by an in vivo method (e.g., by assessing the production of offspring by females into whom the fertilized oocytes are implanted). The method can be used to cryogenically preserve sperm obtained from vertebrates, including mammals and nonmammals, of all types, including sperm obtained from genetically modified vertebrates (e.g., genetically modified mammals, such as genetically modified rodents (e.g., mouse, rat), bovine, canine, feline, swine, goat, sheep, rabbit, horse, camelida, pet or companion mammal) and genetically modified non-mammals (such as genetically modified birds (e.g., chicken, turkey, companion bird) and fish (those produced for consumption, companion fish). Refer to Table 1, which is a list of animals for which the present invention can be used.

In certain embodiments, the method of cryogenically preserving sperm comprises: (a) combining sperm to be cryogenically preserved and a composition that comprises (1) a cryoprotectant, such as one or more sugars (e.g., raffinose, lactose), glycerol and/or propylene glycol; (2) a membrane protectant, which is a macromolecule or mixture of macromolecules that stabilizes or assists in stabilization of membranes of sperm (e.g., milk or milk powder, such as skim milk or skim milk powder; a protein in milk; a milk protein or component thereof); and (3) a free radical scavenger, such as a reducing agent or an antioxidant (e.g., monothioglycerol, reduced glutathione (GSH)), to produce a combination (cryoprotective media-sperm combination); and (b) subjecting the combination to conditions that result in cryopreservation of sperm in the combination, thereby producing a cryopreserved combination that comprises cryopreserved sperm. The macromolecule(s) used can be any macromolecule described herein or any other macromolecule that has the desired characteristics. The initial combination (the combination to be cryopreserved) is produced prior to cryopreservation and can be subjected to conditions that result in cryopreservation of sperm in the combination immediately after it is produced or within a limited period after it is produced. Cryopreservation can be carried out at any time after production that does not significantly adversely affect the viability of the sperm. For example, with mouse or rat sperm, cryopreservation can be carried out at any time within about 90 minutes after it is produced. As a further example, cryopreservation of human or bovine sperm can be carried out up to about 24 hours after production of the combination. Preservation is carried out at a temperature of from about plus 4° C. to about minus 200° C. In specific embodiments, cryopreservation is carried out at a temperature between from about minus 80° C. to about minus 200° C. Before the sperm is incubated with oocytes, the sperm is thawed and may also be washed. In all embodiments described herein, the resulting cryopreserved sperm can be stored indefinitely. The resulting sperm are cryopreserved sperm that exhibit consistently better fertilization potential than the fertilization potential of cryopreserved sperm obtained using presently available methods and media.

The fertilization capacity or ability of sperm can be assessed using methods known to those of skill in the art, such as in vitro, by assessing the ability to fertilize oocytes with which they are combined/incubated (their ability to form 2-cell embryos, for example) and/or in vivo by assessing the production of offspring by females into whom the fertilized oocytes are implanted. In the case of human sperm, fertilization capacity or ability can be assessed using available methods, such as a functional assay, including, but not limited to, a motility assay, a viability assay, a hemizona assay (binding of the sperm to the zona pellucida) or sperm penetration into zona-free hamster oocytes.

In a specific embodiment, the method of cryogenically preserving sperm comprises: (a) combining sperm to be cryogenically preserved and a composition that comprises (1) a cryoprotectant, which is one or more sugars (e.g., raffinose, lactose); (2) a membrane protectant, which is a macromolecule such as a protein (e.g., milk or a protein contained in milk; skim milk or a protein contained in skim milk, egg yolk or a protein contained in egg yolk) that stabilizes or assists in stabilization of membranes of sperm; and (3) a free radical scavenger, such as a reducing agent or an antioxidant (e.g., monothioglycerol, reduced glutathione (GSH)), to produce a combination (cryoprotective media-sperm combination); and (b) subjecting the combination to conditions that result in cryopreservation of sperm in the combination, thereby producing a cryopreserved combination that comprises cryopreserved sperm. The initial combination (the combination to be cryopreserved) is produced prior to cryopreservation and can be subjected to conditions that result in cryopreservation of sperm in the combination immediately after it is produced or within a limited period after it is produced. Cryopreservation can be carried out at any time after production that does not significantly adversely affect the viability of the sperm. For example, with mouse sperm, cryopreservation can be carried out at any time within about 90 minutes after it is produced. Preservation is carried out, for example, at a temperature of from about plus 4° C. to about minus 200° C. In specific embodiments, cryopreservation is carried out at a temperature between from about minus 80° C. to about minus 200° C. In all embodiments described herein, the resulting cryopreserved sperm can be stored indefinitely. The resulting sperm are cryopreserved sperm that exhibit consistently better fertilization potential than the fertilization potential of cryopreserved sperm obtained using presently available methods and media. The fertilization capacity or functionality of sperm can be assessed using methods known to those of skill in the art, such as in vitro, by assessing the ability to fertilize oocytes with which they are combined/incubated (their ability to form 2-cell embryos, for example) and/or in vivo by assessing the production of offspring by females into whom the fertilized oocytes are implanted. In the case of human sperm, fertilization capacity or ability can be assessed using available methods, such as a functional assay, including, but not limited to, a hemizona assay (binding of the sperm to the zona pellucida) or sperm penetration into zona-free hamster oocytes.

In an alternative embodiment, the cryoprotective media includes a (at least one; one or more) cryoprotectant and a (at least one; one or more) free radical scavenger and does not include a membrane protectant. This cryoprotective media, referred to herein as CP-FRS, is useful for the same purposes and in the methods as described herein for CPM.

In one embodiment, the method of cryogenically preserving sperm (producing cryogenically preserved sperm) comprises (a) combining sperm to be cryogenically preserved and a composition that includes a cryoprotectant and a free radical scavenger (such as a reducing agent or an antioxidant), to produce a combination (cryoprotective media-sperm or FRS-sperm combination, also referred to as the initial combination or the combination to be cryopreserved) and (b) subjecting the combination to conditions that result in cryopreservation of sperm in the combination, thereby producing a cryogenically preserved combination that comprises cryogenically preserved sperm.

In a specific embodiment, the method of cryogenically preserving sperm (producing cryogenically preserved sperm) comprises (a) combining sperm to be cryogenically preserved and a composition, referred to as CP-FRS, that includes a cryoprotectant and a free radical scavenger (such as a reducing agent or an antioxidant), to produce a combination (cryoprotective media-sperm combination, also referred to as the initial combination or the combination to be cryopreserved) and (b) subjecting the combination to conditions that result in cryopreservation of sperm in the combination, thereby producing a cryogenically preserved combination that comprises cryogenically preserved sperm.

The initial combination (the combination to be cryopreserved) is produced prior to cryopreservation and can be subjected to conditions that result in cryopreservation of sperm in the combination immediately after production or within a limited period after it is produced. Cryopreservation can be carried out at any time after production that does not adversely affect the viability of the sperm, such as, for mouse sperm, any time within about 90 minutes after it is produced. The resulting sperm are cryopreserved sperm that exhibit consistently better fertilization potential than the fertilization potential of cryopreserved sperm obtained using presently available methods and media. Preservation can be carried out at a temperature of from about plus 4° C. to about minus 200° C. In specific embodiments, cryopreservation is carried out at a temperature between from about minus 80° C. to about minus 200° C. In all embodiments described herein, the resulting cryopreserved sperm can be stored indefinitely at an appropriate temperature, known to those of skill in the art (e.g., at temperatures that range from about minus 80° C. to about minus 200° C.).

The cryoprotectants and free radical scavengers described herein are useful in the CP-FRS composition and methods in which CP-FRS is used. In a further embodiment, the cryopreservation media includes a (at least one, one or more) free radical scavenger and does not include a cryoprotectant or a membrane protectant. In one embodiment, the method of cryogenically preserving sperm (producing cryogenically preserved sperm) comprises (a) combining sperm to be cryogenically preserved and a composition that includes a free radical scavenger (such as a reducing agent or an antioxidant), to produce a combination (cryoprotective media-sperm or FRS-sperm combination, also referred to as the initial combination or the combination to be cryopreserved) and (b) subjecting the combination to conditions that result in cryopreservation of sperm in the combination, thereby producing a cryogenically preserved combination that comprises cryogenically preserved sperm.

In a specific embodiment, the method of cryogenically preserving sperm (producing cryogenically preserved sperm) comprises (a) combining sperm to be cryogenically preserved and a composition, referred to as FRS, that includes a free radical scavenger (such as a reducing agent or an antioxidant), to produce a combination (cryoprotective media-sperm combination, also referred to as the initial combination or the combination to be cryopreserved) and (b) subjecting the combination to conditions that result in cryopreservation of sperm in the combination, thereby producing a cryogenically preserved combination that comprises cryogenically preserved sperm. The initial combination (the combination to be cryopreserved) is produced prior to cryopreservation and can be subjected to conditions that result in cryopreservation of sperm in the combination immediately after production or within a limited period after it is produced. Cryopreservation can be carried out at any time after production that does not adversely affect the viability of the sperm, such as, for mouse sperm, any time within about 90 minutes after it is produced. The resulting sperm are cryopreserved sperm that exhibit consistently better fertilization potential than the fertilization potential of cryopreserved sperm obtained using presently available methods and media. Preservation can be carried out at a temperature of from about plus 4° C. to about minus 200° C. In specific embodiments, cryopreservation is carried out at a temperature between from about minus 80° C. to about minus 200° C. The free radical scavengers described herein are useful in the FRS composition and methods in which FRS is used.

In all embodiments described herein, the resulting cryopreserved sperm can be stored indefinitely at an appropriate temperature, known to those of skill in the art (e.g., at temperatures that range from about minus 80° C. to about minus 200° C.). In all embodiments, the cryoprotective media can comprise additional components, such as water or other solvent, anti-bacterial agent(s), anti-viral agent(s), and/or antibiotic(s).

As used herein, "a" includes "at least one" and "one or more."

In certain embodiments, the method of the present invention is a method of producing live offspring, which can be vertebrates of many types, including mammals and non-mammals. It is a method of producing live offspring, such as rodents (e.g., mouse, rat), cattle/bovine (cows, bulls), dogs, cats, pigs/swine, goats, sheep, horses, camels, rabbits, pet or companion mammals, birds (e.g., chicken, turkey, pet or companion fish (those produced for consumption, companion fish), other species (including endangered species) and humans. The method of producing live offspring comprises the steps described above for cryogenically preserving sperm and further comprises thawing the resulting cryopreserved sperm (thereby producing thawed sperm); introducing thawed sperm or fertilized oocytes produced by using thawed sperm resulting from the method described above into an appropriate female (e.g., a pseudopregnant female, such as a pseudopregnant mouse, when fertilized oocytes are used and a receptive female who is in oestrus, when thawed sperm are used) and maintaining the female into whom oocytes or sperm were introduced under conditions appropriate for growth and development of fertilized oocytes into live offspring (appropriate for production of live offspring), whereby live offspring is/are produced. In those embodiments in which thawed sperm are introduced into an appropriate female, they are present in an appropriate media, such as the CPM or IVF media. For example, the thawed sperm/cryoprotective media combination is undiluted or diluted into an appropriate IVF media (e.g., Cooks Mouse Vitro Fert (Cook Australia; Queensland, Australia; (Quinn et al., 1995)) and introduced into a suitable receptive female. The sperm can be introduced by surgery-assisted artificial insemination (AI). For example, the sperm suspension is transferred by means of a transfer pipette directly into a space between the ovary and ovarian bursa near the infundibulum of an oviduct. Alternatively, the sperm can be inserted into the ampulla region through the oviductal wall of an appropriate receptive female, such as a superovulated female, see (Sato and Kimura, 2001; Sato et al., 2004). Alternatively, the thawed sperm/cryoprotective media combination is diluted into an appropriate IVF media (e.g. Cooks Mouse Vitro Fert (Cook Australia; Queensland, Australia; (Quinn et al., 1995)) and is subsequently mixed with egg masses or oocytes and cultured in vitro to the fertilized egg, 2-cell stage or 4-cell to 16-cell stage embryos, morula or blastocyst stage embryos. Subsequently, fertilized eggs, 2-cell stage or 4-cell to 16-cell stage embryos, morula or blastocyst stage embryos are introduced into an appropriate receptive female.

Also the subject of this invention are cryoprotective media-sperm combinations; cryogenically preserved sperm; and fertilized oocytes, 2-cell embryos and zygotes produced by the methods described.

Also the subject of this invention are non-human live offspring produced by the methods described. In specific embodiments, the live offspring are rodents (e.g., mouse, rat), cows, dogs, cats, pigs/swine, goats, sheep, horses, camels, rabbits, other companion mammals, birds (e.g., chicken, turkey, companion birds), fish (those produced for consumption, companion fish), and other species (including endangered species).

Components of the Cryoprotective Media Cryoprotectant

The cryoprotective media can be varied in its specific components. For example, the cryoprotectant (also referred to as a cryoprotective agent) is typically a non-penetrating cryoprotectant (at least one, one or more non-penetrating cryoprotectant(s)). A penetrating cryoprotectant(s) (at least one, one or more penetrating cryoprotectant(s)) can also be used. A combination of one or more non-penetrating cryoprotectant and one or more penetrating cryoprotectant can be used.

A non-penetrating cryoprotectant is a solute (agent/compound) that is incapable of moving across a cell membrane (here, the membrane of the sperm) to any significant/substantial extent. As a component of the cell suspension, it alters the nature and/or extent of changes that occur within sperm and in the cryoprotective medium to enhance or increase the number (percent) of cells (sperm) that survive cryopreservation. Non-penetrating cryoprotectants useful in the present invention can be a sugar or a nonsugar or a combination of one or more sugars and one or more nonsugars. In specific embodiments, this component of the cryoprotective media is a sugar or combination of two or more sugars. Sugars included in the cryoprotective media can be a disaccharide(s) (trehalose, melibiose, sucrose, lactose), a trisaccharide(s) (e.g., raffinose, melezitose), a tetrasaccharide(s) (e.g. stachyose), an oligosaccharide(s) (mannotriose), or a polysaccharide(s) (e.g., dextran, hydroxyl-ethyl starch (HES)) and sugar alcohols thereof (e.g., maltitol, lactitol). In particular embodiments, the sugar included in the cryoprotective media is raffinose or lactose. Nonsugars, such as polyvinyl pyrrolidone (PVP), polyethylene oxide (PEO) or polyethyleneglycol (PEG), can be included in the cryoprotective media. For example, high molecular weight PEG can be used, such as PEG of any average molecular weight from PEG400 to PEG20000 Dalton (PEG400 to PEG20000). Alternatively, a penetrating cryoprotectant can be used. A penetrating cryoprotectant is a solute (agent/compound) or a solvent that can move across a cell membrane, such as the membrane of the sperm. This component alters the nature and/or extent of changes that occur both within the sperm and in the cryoprotective media to enhance or increase the percent (number) of cells (sperm) that survive cryopreservation.

In specific embodiments, this component of the cryoprotective media is one or more of the following: a penetrating sugar alcohol, such as glycerol; dimethyl sulfoxide (DMSO); an alcohol, such as ethylene glycol or propylene glycol, or a combination of glycerol and propylene glycol. A combination of one or more non-penetrating cryoprotectants and one or more penetrating cryoprotectants can also be used. It should be understood that some components, such as glycerol, act as penetrating or non-penetrating cryoprotectant, depending on the conditions under which they are used. Glycerol is a sugar alcohol that is penetrating at room to body temperature and non-penetrating at temperatures below 0° C. At ambient temperatures, glycerol is a penetrating cryoprotectant.

Membrane Protectant

The membrane protectant component of the cryoprotective media can be any of a wide variety of macromolecules that act as a buffer and diluent to stabilize or assist in stabilizing cell membranes. The membrane protectant component can be a (one or more, at least one) protein, a (one or more, at least one) non-protein or a combination of a protein or proteins and a non-protein or non-proteins. The one or more proteins can be present in/derived from animal sources (animal proteins) and can be, for example, milk, milk derivatives or components, such as milk protein, skim milk (such as liquid skim milk or skim milk powder), a protein in milk (e.g., in whole milk, skim milk) or a component of a milk protein; casein, egg, egg yolk, egg white (e.g. fresh egg, egg yolk or egg white, such as fresh chicken egg, egg yolk or egg white), a protein in egg, egg yolk or egg white; collagen, elastin, gelatin, atelocollagen, fibronectin, peptones, keratin, albumin or any combination thereof. Alternatively, the one or more proteins can be derived from plant sources (plant proteins) and can be, for example, soy protein, wheat protein, corn protein, coconut milk, Aloe vera extract, jojoba extract, or any combination thereof. The membrane protectant can be a combination of one or more animal proteins and one or more plant proteins. The one or more proteins can be a recombinantly produced protein, such as casein, collagen, gelatin, fibronectin, albumin, lactalbumin, lactoglobulin, keratin or any combination thereof. Alternatively, the membrane protectant can be a lipid (e.g., animal lipid, plant lipid, chemically synthesized), synthetic lipids, such as phosphatidylglycerol, phosphatidic acid, 1,1',2,2'-tetra-acyl-cardiolipin, phosphatidylcholine, phosphatidylserine, phosphatidylethanolamine, polyoxyethylene based lipids, arachidonic linoleic, linolenic, myristic, oleic, palmitic or stearic fatty acids, cholesterol, Pluronic F-68 or any combination thereof can be used (e.g., as in chemically defined lipid concentrate supplies by Invitrogen Cat. No. 11905-031 or lipid mixture 1 by Sigma, Cat. No. L0288). A further example of a membrane protectant is a polymer, polyvinylalcohol (PVA). Any combination of the membrane protectants described herein or similar agents can be used in the cryoprotective media. For example, one or more proteins, such as one or more proteins of animal origin and/or one or more proteins of plant origin and/or one or more recombinant protein can be included in the cryoprotective media, which can also comprise additional membrane protectants, such as one or more lipids (e.g., one or more lipids of animal origin and/or one or more lipids of plant origin and/or one or more synthetic lipid, any mixture of these types of lipids) and/or PVA. The concentration of the membrane protectant can be determined empirically, using methods known to those of skill in the art. In certain embodiments, the concentration of membrane protectant is from about 1% weight/volume to about 50% weight/volume, such as 3% weight/volume for skim milk powder. Alternatively, the concentration can be from about 1% volume/volume to about 90% volume/volume, such as 23% volume/volume for egg yolk and 90% for milk. In all embodiments, the concentration can be any concentration within these ranges.

Free Radical Scavenger

The free radical scavenger component (also referred to as a free radical scavenger agent) of the cryoprotective media can be any scavenger which is compatible with viability of sperm and sufficiently effective (active) that it removes or inactivates free radicals (reactive oxygen species) in the combination to such an extent that the percent (number) of cells (sperm) that survive cryopreservation and can fertilize oocytes is consistently enhanced. A free radical scavenger component can be any compound or molecule, such as a reducing agent or an antioxidant, that has these desired characteristics. Useful free radical scavenger agents can be identified as described in Example 4 and Example 13, in which the ability of monothioglycerol to act as reducing agent was assessed using a fluorescent dye and flow cytometry. Free radical scavenger agents useful in the cryoprotective media of the present invention can alternatively be identified by methods known to those of skill in the art.

One or more free radical scavengers (e.g., one or more reducing agent(s) and/or one or more antioxidants) can be included in the cryoprotective media. In specific embodiments, the free radical scavenger can be, for example, one or more reducing agents, such as one or more of the following: monothioglycerol (MTG), beta-mercaptoethanol, dithiothreitol (DTT), Tris (2-carboxyethyl) phosphine (TCEP), dithioerythritol, thioredoxin (TRX), dithionite, 2-mercaptoethylamine, dimethyl thiourea; nordihydroguaiaretic acid (NDGA), 2,3-dimercapto-1-propanol or hydroquinone. Alternatively, the free radical scavenger can be one or more antioxidants, such as one or more of the following: an amino acid or derivative thereof (e.g., reduced glutathione (GSH), cysteine, homocysteine, N-acetyl cysteine (NAC), methionine, N-2-mercaptopropionyl glycine, alanine, glutathionine), bilirubin, melatonin, mannitol, lipoic acid, 10,11-dihydroxyaporphine (DHA), butylated hydroxyanisole (BHA), butylated hydroxytoluene, dihydroolipoic acid, tetrahydropapaveroline (THP), 2-thiobarbituic acid, or taurine, and dimercaptosuccinic acid inositol. Further, the free radical scavenger can be a vitamin (such as vitamin E (tocopherol or a derivative thereof, such as water soluble forms of vitamin E; vitamin C (ascorbic acid); vitamin A, carotenoids, (Astaxanthin), vitamin B complex (including inositol) or Coenzyme Q); allopurinol, dimethyl sulfoxide, deferoxamine, an enzyme (such as catalase, glutathione peroxidase or superoxide dismutase), a steroid (such as 21-aminosteroids, methylprednisolone), or glutathionine.

In a specific embodiment of the cryoprotectant media, the free radical scavenger is monthioglycerol. In this embodiment, the free radical scavenger is typically present in the cryoprotective media at a level of from about 50 μM to about 50 mM (50000 μM). Any level between from about 50 μM to about 50 mM (50000 μM) monothioglycerol can be used. In a further embodiment, the free radical scavenger is reduced glutathione (GSH). In this embodiment, the free radical scavenger is typically present in the media at a level of from about 50 μM to about 50 mM. Any level between from about 50 μM to about 50 mM (50000 μM) GSH can be used. The concentration of other free radical scavengers can be determined empirically and will vary depending on the particular agent used.

In a specific embodiment of the cryoprotective media, the cryoprotectant is a sugar (e.g., raffinose or lactose), or a sugar alcohol (e.g., glycerol), or an alcohol (e.g., propylene glycol), or combination of two or more of the preceding (e.g. lactose and/or raffinose and propylene glycol or lactose and/or raffinose and glycerol); the membrane protectant is a macromolecule, such as a milk or milk protein (such as skim milk protein) or skim milk or egg yolk; and the free radical scavenger is a reducing agent, such as monothioglycerol, or an antioxidant, such as GSH.

In an alternative embodiment of the cryoprotective media (CP-FRS), the cryoprotectant is a sugar (e.g., raffinose, or lactose), or a sugar alcohol (e.g., glycerol), or an alcohol (e.g., propylene glycol), or a combination of two or more of the preceding (e.g., lactose and/or raffinose and propylene glycol or lactose and/or raffinose and glycerol) and the free radical scavenger is a reducing agent, such as monothioglycerol or dithiothreitol, or an antioxidant, such as GSH.

In further specific embodiments, the (at least one; one or more) sugar is raffinose or lactose; the (at least one; one or more) membrane protectant is a macromolecule, such as a milk; and the (at least one; one or more) reducing agent is monothioglycerol (MTG). In further specific embodiments, the (at least one) sugar is raffinose; the (at least one) macromolecule is a milk protein; and the (at least one) antioxidant is GSH. Alternatively, the (at least one; one or more) membrane protectant is skim milk.

In further specific embodiments, the cryoprotectant is a (at least one; one or more) sugar, such as lactose or a sugar alcohol, such as glycerol or an alcohol, such as propylene glycol; the (at least one; one or more) membrane protectant is egg yolk (e.g., fresh egg yolk, such as fresh chicken egg yolk) or skim milk; and the (at least one; one or more) free radical scavenger is monothioglycerol (MTG) or reduced glutathione or dithiothreitol (DTT). In further specific embodiments, the (at least one; one or more) sugar is raffinose; the (at least one; one or more) macromolecule is skim milk or a milk protein; and the (at least one; one or more) free radical scavenger is GSH, MTG or DTT.

In a specific embodiment, the method of the present invention is a method of cryogenically preserving sperm, comprising combining sperm with cryoprotective media which comprises at least one sugar; at least one membrane protectant (e.g., a macromolecule such as a protein or a polymer); and at least one free radical scavenger, such as a reducing agent or an antioxidant. The at least one sugar can be any of the sugars described herein; the membrane protectant is a polymer, such as polyvinylalcohol or Pluronic F-68; and the at least one free radical scavenger agent can be any reducing agent or any antioxidant described herein or a combination of one or more reducing agents and one or more antioxidants.

The quantities and relative concentrations of each of these components of the cryoprotective media (cryoprotectant, membrane protectant, free radical scavenger), as well as the quantities and relative concentrations of other media components (e.g., water) can be determined empirically, using methods known to those of skill in the art, for production of a variety of media. See the examples.

Methods of Preserving Sperm

The cryopreservation media and methods of the present invention can be used for preserving sperm from a wide variety of mammals and in specific embodiments, is used for cryopreservation of rodent sperm, such as mouse or rat sperm; bovine sperm or human sperm. As discussed in greater detail below, the media and methods can be used with any strain/substrain or stock of mouse. In specific instances, the composition of the cryopreservation media may be adjusted as to its components and/or their respective concentrations, in order to enhance the effectiveness of the media in protecting the particular type of sperm (e.g., adjusted to suit the particular strain of mouse sperm) from cryopreservation. Adjustments can be made empirically, using methods known to those of skill in the art. For example, the mouse strain can be either inbred (e.g., C57BL/6; BALB/c; FVB/N; 129S3/SvIm) or outbred stock.

The cryoprotective media and methods of this invention are particularly useful for cryopreservation of mouse sperm, such as sperm from inbred mouse strains, particularly the C57BL mouse strains, such as C57BL/6, and, thus, for production of live mice of all types and strains, such as live C57BL offspring, such as live C57BL/6 offspring. The method can be used to produce live offspring from all mice with C57BL background, such as C57BL/6 strains and particularly C57BL/6 offspring (e.g., genetically modified transgenics, knockouts, as well as, but not limited to, live 129 offspring, live FVB offspring and live BALB/c offspring. See, for example, Tables 3A and 3B).

Sperm which are processed by the method and using the cryoprotective media of the present invention can be non ejaculate, such as that obtained as described herein, or ejaculate sperm. The cryoprotective media-sperm combination can be placed into vials, cryotubes, glass ampoules, ministraws or straws for cryopreservation and subsequent storage. The quantity or concentration of sperm to be used can be determined empirically, using known methods, taking into consideration such factors as the type of sperm and the type, size and shape of the container being used. In the instances in which mouse sperm is being cryopreserved or used, 0.3× to 3× of sperm per 10 microliters of CPM or CP-FRS are generally used. The concentration 1× is defined such that the sperm from one male are collected into 1 mL of CPM or CP-FRS. In the case of C57BL/6 mice, this is a concentration in the range of $31.5\pm2.8\times10^6$ sperm/mL. For other strains and species, the optimal concentration may be different from that for C57BL/6 sperm and can be empirically determined using techniques known to the person skilled in the art.

Kits

In another aspect, the present invention provides any of the compositions described herein in kits, optionally including instructions for use of the compositions (e.g., for preserving sperm and/or other cells). That is, the kit can include a description of use of a composition in any method described herein. A "kit," as used herein, typically defines a package, assembly, or container (such as an insulated container) including one or more of the components of the invention, and/or other components associated with the invention, for example, as previously described. Each of the components of the kit may be provided in liquid form (e.g., in solution), or in solid form (e.g., a dried powder, frozen, etc.).

In some cases, the kit includes one or more components, which may be within the same or in two or more receptacles, and/or in any combination thereof. The receptacle is able to contain a liquid, and non-limiting examples include bottles, vials, jars, tubes, flasks, beakers, or the like. In some cases, the receptacle is spill-proof (when closed, liquid cannot exit the receptacle, regardless of orientation of the receptacle).

In some embodiments, a kit may comprise two or more of: a membrane protectant, a free radical scavenger, and a cryoprotective agent, which may be in the same receptacle, or divided among two or more receptacles. As a specific, non-limiting example, a first receptacle may contain at least two of: the membrane protectant, the free radical scavenger, and the cryoprotective agent, while a second receptacle may contain a component that is not present in the first vessel. In some cases, the components of the kit may be contained within a suitable container, such as a cardboard box, a Styrofoam box, etc. The kit may be shipped at room temperature (about 25° C.), chilled (e.g., at about 4° C.), and/or any one or more of the components may be shipped frozen (e.g., between −20° C. and −80° C., at about −150° C., etc.) or in liquid nitrogen (about −196° C.). In some cases, one or more of the components are frozen and/or shipped on dry ice (about −80° C.).

With regard to frozen solutions, if more than one component is present (e.g., as described above), the components may be frozen together in one common liquid (e.g., within one common receptacle), or as two or more separate liquids (e.g., within separate receptacles).

In certain cases, some of the components may be processable (e.g., to an active form), for example, by the addition of a suitable solvent or other species, which may or may not be provided with the kit. For example, the component may be heated or a liquid may be added to the component (e.g., if the component is frozen, lyophilized, shipped in a concentrated form, etc.).

In one embodiment, the kit for use in cryopreserving sperm comprises at least one cryoprotectant; at least one free radical scavenger; and at least one membrane protectant. In a specific embodiment, the free radical scavenger was identified by a method described herein. In other embodiments, the kit comprises at least one cryoprotectant and at least one free radical scavenger.

In some cases, the kit will include a cryogenic vessel which is a vessel suitable for containing materials at cryogenic temperatures, for example, liquid nitrogen. Those of ordinary skill in the art will be aware of suitable cryogenic vessels, for example, a Dewar flask (e.g., formed from stainless steel and/or aluminum, etc.), a vapor shipper, a stainless steel container, a Styrofoam container, or the like. Typically, cryogenic temperatures include temperatures below about −150° C., below about −170° C., or below about −190° C. For instance, liquid nitrogen has a boiling point of about −196° C.

The kit may also contain a receptacle for holding sperm and/or other cells. In some cases, this receptacle is able to contain the liquid containing the sperm, and/or a frozen solution or liquid containing the sperm. For example, the receptacle may be constructed so that it can withstand cryogenic temperatures without rupture or fracture. In some embodiments, the receptacle can be placed within a cryogenic vessel, as described above, (e.g., using a float (for example, that can float on liquid nitrogen or other cryogenic liquid within the cryogenic vessel)). Non-limiting examples of receptacles for sperm and/or other suitable cells include cell straws, glass ampoules, cryotubes, cryovials, etc. The receptacle may be pre-labeled in certain instances.

Examples of other compositions or components associated with the invention include, but are not limited to, diluents, salts, buffers, chelating agents, preservatives, drying agents, antimicrobials, needles, syringes, packaging materials, tubes, bottles, flasks, beakers, and the like, for example, for using, modifying, assembling, storing, packaging, preparing, mixing, diluting, and/or preserving the components for a particular use. In embodiments where liquid forms of any of the components are used, the liquid form may be concentrated or ready to use.

A kit of the invention generally will include instructions or instructions to a website or other source in any form that are provided for using the kit in connection with the components and/or methods of the invention. For instance, the instructions may include instructions for the use, modification, mixing, diluting, preserving, assembly, storage, packaging, and/or preparation of the components and/or other components associated with the kit. In some cases, the instructions may also include instructions for the delivery of the components, for example, for shipping at room temperature, sub-zero temperatures, cryogenic temperatures, etc. The instructions may be provided in any form that is useful to the user of the kit, such as written or oral (e.g., telephonic), digital, optical, visual (e.g., videotape, DVD, etc.) and/or electronic communications (including Internet or web-based communications), provided in any manner.

As used herein, instructions can include protocols, directions, guides, warnings, labels, notes, and/or "frequently asked questions" (FAQs), and typically involve written instructions on or associated with the invention and/or with the packaging of the invention. Instructions can also include instructional communications in any form (e.g., oral, electronic, digital, optical, visual, etc.), provided in any manner (e.g., within or separate from a kit) such that a user will clearly recognize that the instructions are to be used with the kit.

As an example, a kit as discussed herein may be shipped to a user, typically with instructions for use. For instance, the instructions may instruct the user to add sperm to the membrane protectant and the free radical scavenger, and store the resulting combination and/or return the kit and the sperm to the sender. As another example, the instructions may instruct the user to combine of sperm, membrane protectant, free radical scavenger, and cryoprotective agent, and cryopreserve the resulting combination (e.g., as described above). The cryopreserved combination could then be stored, returned to the shipper for storage and later recovery, or the like.

Identification of Free Radical Scavengers

One embodiment is a method of identifying a free radical scavenger suitable for use in cryopreserving sperm, comprising assessing at least one of the following activities of a candidate free radical scavenger: (a) capability (ability) to reduce reactive oxygen species in sperm; (b) effect of sperm motility; and (c) effect on in vitro fertilization, wherein if the candidate free radical scavenger produces a beneficial effect on at least one of (a), (b) or (c), the candidate free radical scavenger is a free radical scavenger. For example, if there is a reduction in reactive oxygen species in sperm when the sperm are contacted, combined or incubated with a candidate free radical scavenger, the candidate free radical scavenger is a free radical scavenger suitable for use in cryopreserving sperm. If sperm motility is enhanced or at least maintained at substantially the same level as prior to cryopreservation, when the sperm are contacted, combined or incubated with a candidate free radical scavenger, the candidate free radical scavenger is a free radical scavenger suitable for use in cryopreserving sperm. If in vitro fertilization is enhanced or at least maintained at substantially the same level as prior to cryopreservation, when the sperm are contacted, combined or incubated with a candidate free radical scavenger, the candidate free radical scavenger is a free radical scavenger suitable for use in cryopreserving sperm. In one embodiment, if a free radical scavenger to be identified is a free radical scavenger for use in cryopreserving mouse sperm, activity (a) and/or activity (c) are assessed. In one embodiment, if a free radical scavenger to be identified is a free radical scavenger for use in cryopreserving bovine sperm, activity (a) and/or activity (b) are assessed. The method can be carried out using a variety of approaches to detecting the effect, if any, of a candidate free radical scavenger, such as a method in which a dye is used. In one embodiment, the method comprises incubating (a) sperm loaded with a cell-permeant indicator (dye) for reactive oxygen species that is nonfluorescent unless oxidation occurs within the sperm and (b) a candidate free radical scavenger, thereby producing an incubated combination and assessing the level of reactive oxygen species within sperm in the incubated combination. If the level of reactive oxygen species in the sperm is reduced (e.g., relative to the level of reactive oxygen species within the sperm in the absence of the candidate free radical scavenger), the candidate free radical scavenger is a free radical scavenger suitable for use in cryopreserving sperm. A free radical scavenger identified by assessment of one or two of the three activities described above, can be further assessed for its usefulness as a free radical scavenger by assessing the additional activities. For example, if capability (ability) to reduce reactive oxygen species in sperm is assessed, the effect of the free radical scavenger on sperm motility, its effect of the in vitro fertilization; or both can be assessed, as appropriate, to provide further indication of the suitability of the free radical scavenger for use in cryopreservation of sperm.

EXAMPLES

The following examples describe use of the media and methods of the present invention. They are not intended to be limiting in any way.

Example 1

Cryopreservation of Mouse Sperm

Historic reports have detailed that live born recovery rates when cryopreserved C57BL/6 sperm are used typically range from 0% to less than 10% (Glenister and Thornton, 2000). Nagakata reports a fertilization rate of 26% (Nakagata and Takeshima, 1993). Applying very complex procedures like the two-step method to select for higher quality sperm at thawing by (Bath et al 2003 improve the fertilization rates, but are not adequate for efficient banking (including recovery) of large numbers of C57BL/6 strains via cryopreserved sperm.

The Jackson Laboratory has been working on developing a viable, economical approach to archive inbred and especially C57BL/6 strains. Described herein is a modified cryoprotective media (CPM) that provides an economical approach to this problem.

TABLE 2

Comparison of Cryopreservation Approaches: Characterization and Fertilization Capacity of C57BL/6J Sperm.

| CPM | Post-thaw % Intact Acrosomes | Post-thaw % Intact Membranes | % 2-Cell |
|---|---|---|---|
| Traditional method | 16.1 ± 0.06 | 22.5 ± 0.08 | 7.03 ± 0.35[b] |
| CPM method | 16.8 ± 0.13 | 26.4 ± 0.22 | 19.2 ± 0.26[a] |

CByB6F1 females were used for oocyte donation. Comparisons of percents were made using an arcsine transformation; percents within a column having unique superscript (a and b) are different with Tukey-Kramer HSD (p<0.05); (see Table 2). Table 2 shows that no measurable differences were noted in mouse sperm viability or in the percentage of live spermatozoa having intact acrosomes, but that there is a significant difference in the mouse sperm fertilization rate (% 2-cell) with 19% using the CPM versus 7% using the traditional method.

Applicants have shown that fertilization rates are greatly and consistently improved when the media and methods described herein are carried out. The epididymides and vas deferentia are extracted from the C57BL/6J male and placed into the cryoprotective media described herein. They are extracted and placed into an incubated 1 mL collection drop of CryoProtective Medium (CPM), which comprises, for example, raffinose [18% w/v], skim milk [3% w/v] and monothioglycerol (MTG) at concentrations from 159 μM to 636 μM. Incisions are made in the tissues, allowing the sperm to swim out into the CPM; this is allowed for at least 5 but for less than 20 min. The residual tissues are then removed from the collection drop. Ten micro liters of the sperm sample are loaded into as many as one hundred 250 μL French straws (IMV; Maple Grove, Minn.). Two hundred and fifty microliter straws, containing a 5.5 cm column of CPM, a 2.5 cm column of air, a 0.6 cm column of sperm sample followed by a column of air, are sealed with an instantaneous heat sealer. The straws are loaded into cassettes and exposed to liquid nitrogen vapor for at least 10 min before being plunged into the liquid nitrogen. This essentially cools the sperm at 37° C./min.

Subsequent to storage in liquid nitrogen, 3 samples from each treatment are thawed in a 37° C. water bath for 30 sec, and then each 10 μL aliquot is placed directly into its own 500 μL in vitro fertilization (IVF) drop of Cooks Mouse Vitro Fert (Cook Australia; Queensland, Australia). After an hour of incubation, 4 cumulus intact oocyte clutches from superovulated C57BL/6J females are added to the in vitro fertilization drops. IVF is carried out using methods known to those of skill in the art, such as by the methods described by Nakagata. (Nakagata, 2000a; Nakagata, 2000b). The sperm and oocytes are incubated together for 4 hrs before the presumptive zygotes are removed from the IVF drop and placed in a culture drop for overnight incubation.

Approximately 18 hours later, the percentage of oocytes developing into 2-cell embryos is determined (#2-cell embryos/4 total oocytes). For statistical analysis, percents are arcsine transformed and the averages of at least 3 IVF drops per treatment are evaluated with a T-Test. A difference between treatments is illustrated with an asterisk (p<0.05). For presentation, means and standard errors were converted back into percents.

All concentrations of MTG show an improved fertilization rate, relative to results obtained using presently-available methods. An MTG concentration of 477 μM provided the best results. See FIG. 1 and Table 3 and Table 4A.

TABLE 3

Fertilization Rate using C57BL/6J Mice and Either CPM or Traditional Method

| | Fertilization Rate | 2-Cell Embryos Transferred | Live Born |
|---|---|---|---|
| CPM | 68.4% | 225 | 80 |
| Traditional method | 6.5% | 45 | 7 |

The following day the 2-cell embryos can be transferred to pseudopregnant recipients or cryopreserved for later use.

Previous methodologies have provided fertilization rates of lower than 10% (Songsasen and Leibo, 1997; Szczygiel et al., 2002; Sztein et al., 2001; Thornton et al., 1999) when using cryopreserved C57BL/6J sperm in standard IVF procedure without any manipulation of the oocyte and without preselection of the sperm, not using intracytoplasmic sperm injection (ICSI). There is only one report which claims to have achieved 26% fertilization rate for C57BL/6J (Nakagata and Takeshima, 1993). Employing the approach described herein, which includes the use of free radical scavenger, fertilization rates of greater than 75% have been obtained. These methods have also greatly and consistently improved the fertilization rates observed for other mouse strains as well. For example, using previous methods it was not uncommon to find fertilization rates for BALB/cJ, FVB/NJ, and 129P3/J to be less than 10%, 30% and 5%, respectively.

Mice referred to herein as 129P3/J were referred to in the priority applications as 129P/J mice. This is only a change in nomenclature. The method described herein has resulted in observed fertilization rates of 58%, 98% and 48%, respectively. See Tables 4A and 4B.

TABLE 4A

Assessment of Fertility Rates in Different Mouse Strains

| Treatment | Strain | | | | | | |
|---|---|---|---|---|---|---|---|
| | 129X1/SvJ | 129S1/SvImJ | BALB/cByJ | BALB/cJ | C3H/HeJ | FVB/NJ | C57BL/6J |
| | | | | Mean Fertilization Rate | | | |
| CPM + MTG | 51.2% | 18.5% | 69.1% | 58.4% | 99.0% | 98.6% | 68.4% |
| | (81/158) | (80/425) | (231/177) | (153/290) | (301/307) | (203/209) | (326/488) |
| Traditional Method | 21.7% | 0.0% | 7.0% | 10.3% | 55.3% | 27.4% | 6.5% |
| | (93/428) | (0/36) | (39/521) | (144/1299) | (150/327) | (203/607) | (227/1581) |

TABLE 4B

Assessment of Fertility Rates in Different Mouse Strains

| Mouse Strain | CPM (+MTG) | Traditional Method |
|---|---|---|
| 129P3/J | 48.20% | 12% (Songsasen and Leibo, 1997) |
| A/J | 92.67% | no data |
| CAST/EiJ | 2.38% | 0% |
| DBA/2J | 87.85% | 45% |
| FVB/NJ | 98.6% | 27.4% |
| NOD/LtJ | 75.21% | no data |
| SJL/J | 46.56% | no data |

Example 2

Cryopreservation of Mouse Sperm with CPM Containing GSH

Applicants have shown that fertilization rates are greatly and consistently improved when the media and methods described herein are carried out. The epididymides and vas deferentia are extracted from the C57BL/6J male and placed into the cryoprotective media described herein. They are extracted and placed into an incubated 1 mL collection drop of CryoProtective Medium (CPM), composed of raffinose [18% w/v], skim milk [3% w/v] and reduced glutathione [GSH; 500 μM to 50 mM]). Incisions are made in the tissues, allowing the sperm to swim out into the CPM; this is allowed for at least 5 but for less than 20 min. The residual tissues are then removed from the collection drop. Ten micro liters of the sperm sample are loaded into as many as one hundred 250 μL French straws (IMV; Maple Grove, Minn.). Two hundred and fifty microliter straws, containing a 5.5 cm column of CPM, a 2.5 cm column of air, a 0.6 cm column of sperm sample, followed by a column of air, are sealed with an instantaneous heat sealer. This essentially cools the sperm at 37° C./min. After being stored in liquid nitrogen, 3 samples from each treatment are thawed in a 37° C. water bath for 30 sec, and then each 10 μL aliquot is placed directly into its own 500 μL in vitro fertilization (IVF) drop of Cooks Mouse Vitro Fert (Cook Australia; Queensland, Australia). After an hour of incubation, 4 cumulus intact oocyte clutches from superovulated C57BL/6J females are added to the in vitro fertilization drops. (Nakagata, 2000a; Nakagata, 2000b).

The sperm and oocytes are co-incubated for 4 hrs before the presumptive zygotes are removed from the IVF drop and placed in a culture drop for overnight incubation.

Figure 2:
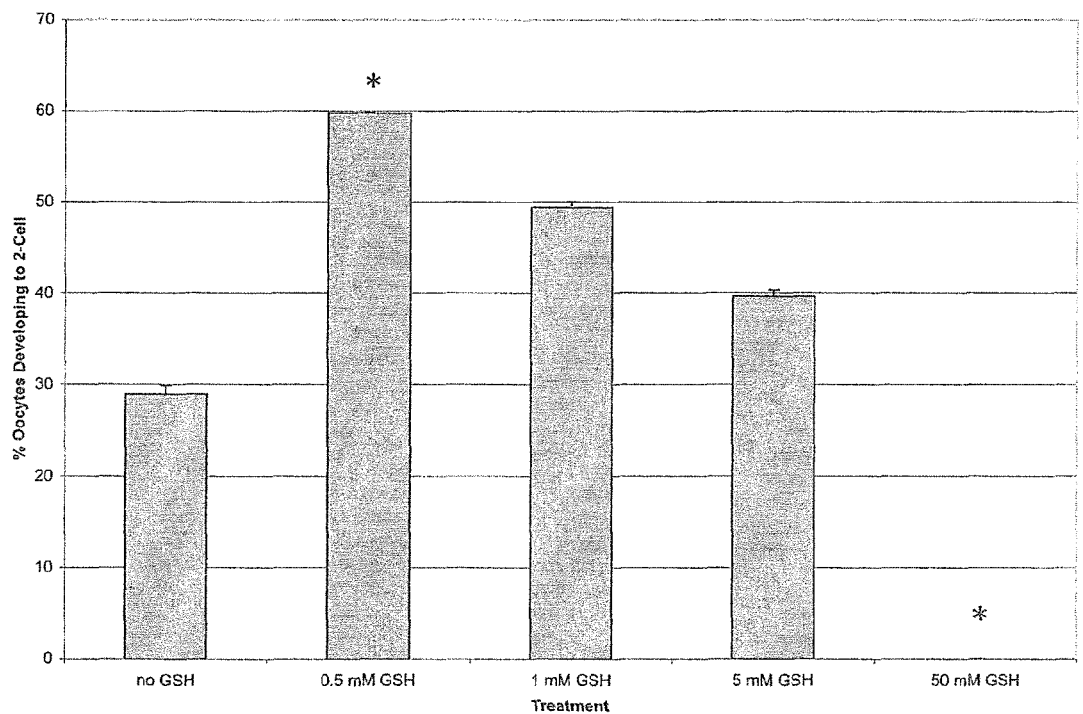
FIG. 2 illustrates that GSH enhances the fertility of cryopreserved C57BL/6J sperm.

Approximately 18 hours later, the fertilization rate is determined (#2-cell embryos/# total oocytes). For statistical analysis, percents are arcsine transformed and the averages of the 3 IVF drops per treatment are compared to the control of no GSH using Dunnett's methods. Results are presented in FIG. 2. A significant difference from the control is illustrated with an asterisk. For presentation, means and standard errors are converted back into percents.

Testing different concentrations of GSH reveals that the concentrations from 500 μM to 5 mM increase the fertilization rates compared to CPM without a reducing agent. Use of 500 μM GSH shows an enhancement in fertilization rates similar to those obtained with 477 μM MTG under similar conditions.

Example 3

Fertilization Rates with Cryopreserved Sperm from Various Mouse Strains Differ in Response to Cryopreservation with MTG Ten μL aliquots of sperm from a variety of mouse strains are frozen in the absence (CPM-MTG) or presence of monothioglycerol (CPM). A total of at least 6 sperm samples per treatment within a strain are utilized. These represented at least 3 samples from each of at least 2 sets of 2 males whose sperm are pooled at the time of collection and then split into the two treatments. Subsequent to thawing, the samples are placed directly into their own 500 μL in vitro fertilization (IVF) drop of Cooks Mouse Vitro Fert (Cook Australia; Queensland, Australia; (Quinn et al., 1995)). After an hour incubation, 4 cumulus intact oocyte clutches from isogenic strains are added to the incubation medium. Following a 4 hr co-incubation, the presumptive zygotes are washed and cultured overnight. Approximately 18 hours later, the fertilization rate is determined (#2-cell embryos/# total oocytes). See Table 5.

TABLE 5

Fertilization Rates Determined in the Presence
(CPM) and Absence of MTG (CPM-MTG)

| Treatment | Strain | | |
|---|---|---|---|
| | 129S1/SvImJ | BALB/cJ | C57BL/6J |
| | Fertilization Rate | | |
| CPM-MTG | 31.1% | 46.2% | 49.0% |
| CPM | 48.1% | 58.4% | 68.4% |

Example 4

Figure 3:
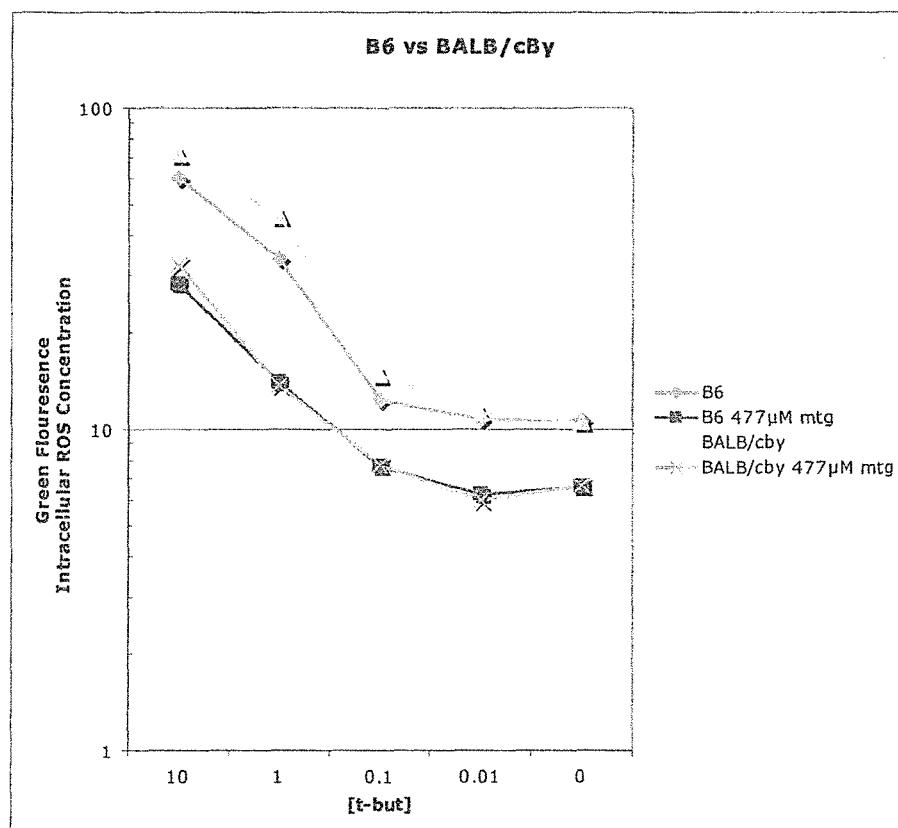
FIG. 3 illustrates that MTG reduces the ROS in cryopreserved sperm from both C57BL/6J (B6) and BALB/cByJ (BALB/cBy) mice.

Assessment of Reduction of Reactive Oxygen Species (ROS) by MTG Description of Free Radical Scavenger by Dye/Sperm Method Sperm cryopreserved in the presence and absence of the free radical scavenger, the reducing agent monothioglycerol (MTG), are loaded with the green fluorescent dye CM-H2DCFDA to measure intracellular reactive oxygen species. The sperm are challenged with varying levels of Tert-Butylhydrogen peroxide to induce oxidative damage and green fluorescence is measured using flow cytometry. As shown in FIG. 3, MTG reduces the ROS in cryopreserved sperm from both C57BL/6J (B6) and BALB/cByJ (BALB/cBy) mice.

Example 5

Cryopreservation and Recovery of Sperm from Genetically Modified Mouse Strains

The same approaches have been carried out on sperm obtained from C57BL/6J males having genetic modifications and variable genetic contributions from the 129 strain, as well as other strains, such as FVB/N.

Ten μL aliquots of sperm from a number of genetically modified mouse strains are frozen in CPM with 477 μM monothioglycerol as the free radical scavenger (CPM) according to the method as described in Example 1. For a transgenic mouse carrying a YAC expression construct, sperm from the strain Tg(YAC72)2511Hay on the FVB/NJ background was collected. For mice carrying modifications due to gene targeting (knockout) sperm from the mouse strains PLAU knockout, glycogen synthase kinase 3β knockout and solute carrier family 22 organic/anion cation transporter member 12 knockout was collected. The strain background means here a contribution of 50% or more of this strain to the genetic background of the mouse strain. The fertilization rate was determined (#2-cell embryos/# total oocytes) and the average percentage was calculated. The values within the parentheses illustrate the total # of two cells/the total number of oocytes across IVFs. As shown in Table 6, high fertilization rates have been obtained in all cases. This demonstrates that cryobanking male mouse germplasm for strain reconstitution is a viable option.

TABLE 6

Fertilization Capacity of Sperm from Genetically Modified Mice

| JR Reference No. | Strain Background | Genetic Modification | % 2-Cell Stage (# 2-cell/# oocytes) |
|---|---|---|---|
| 3640 | FVB/NJ | Tg(YAC72)2511Hay transgene | 81 (105/130) |
| 3238 | BALB/cJ | C2ta (class II transactivator) knockout | 76 (112/148) |
| 2329 | FVB/NJ | PLAU (plasminogen activator, urokinase) knockout | 86 (151/176) |
| 5817 | C57BL/6J | Glycogen synthase kinase 3β knockout | 65 (72/111) |
| 5839 | C57BL/6J | Solute carrier family 22 organic/anion cation transporter member 12 knockout | 68 (53/78) |

Example 6

Determination of Sperm Concentration and Motility

To determine the concentration, motility, and progressive motility of "freshly-collected" sperm, the sperm is typically diluted 1:20 in either phosphate buffered saline or Cooks Mouse Vitro Fert (Cook Australia; Queensland, Australia; (Quinn et al., 1995)). To assess thawed sperm, sperm is incubated in IVF medium for an hour, at a dilution of 1:50 in the IVF drop. It is then loaded into a Hamilton Thorn IVOS computerized semen analyzer (Hamilton Thorn, Beverly, Mass.). For measurement, the calibration parameters are set as follows:

| | |
|---|---|
| Apply Sort: | 2 |
| Frames acquired: | 30 |
| Frame rate: | 60 Hz |
| Minimum contrast: | 30 |
| Minimum Cell Size: | 4 pixels |
| Minimum Static Contrast: | 15 |
| Straightness (STR), Threshold: | 50% |
| Low VAP Cutoff: | 10.0 μm/s |
| Medium VAP Cutoff: | 50.0 μm/s |
| Low VSL Cutoff: | 0.0 μm/s |
| Head Size, Non-Motile: | 13 pixels |
| Head Intensity, Non-Motile: | 75 |
| Static Head Size: | 0.57 to 2.91 |
| Static Head Intensity: | 0.14 to 1.84 |
| Static Elongation: | 0 to 87 |
| Slow Cells Motile: | YES |
| Magnification: | 0.82 |
| Video Source: | Camera |
| Video Frequency: | 60 |
| Bright Field: | No |
| Brightness for LED: | 2663 |
| Brightness for Ident: | 3000 |
| Temperature, Set: | 37° C. |
| Cell Type: | User |
| Cell Depth Setup: | 100.0 μm |
| Field Selection Mode: | SELECT |
| Ident Active: | NO |
| Ident Mode: | B |
| Integrating Time: | 1 Frames |
| Optics | |
| Video Gain: | Medium |
| Video Brightness: | 2300 |
| Video Contrast: | 40 |
| Video Sync Level: | FW Sync_Level_100 |
| Video Vertical Sync: | 75 |

-continued

| Sort #2 | |
|---|---|
| Points in Track: | 16 to 100 |
| Track Speed (VCL): | 146.0 to 1000.0 |
| Linearity (LIN): | 0.0 to 20.0 |

Example 7

Assessment of Sperm Fertilization Capability After Cryopreservation

Figure 4:
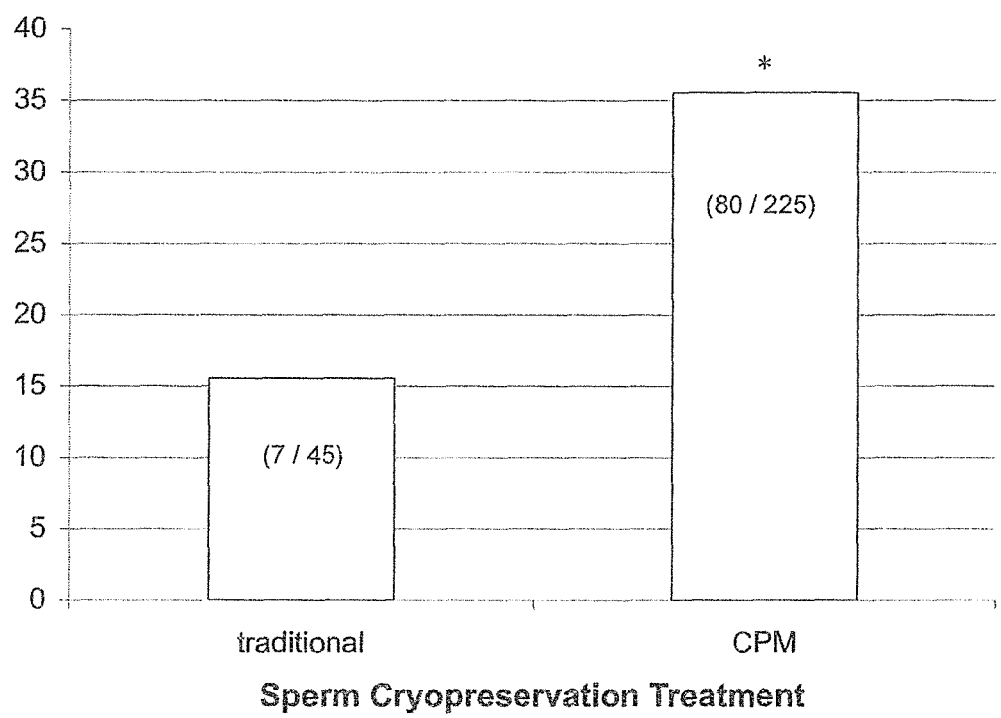
FIG. 4 illustrates an enhancement of sperm fertilization capability after cryopreservation.

To ensure that the enhancement in C57BL/6J sperm fertilization capability post cryopreservation is not just to the development of two cell embryos, Applicants also transferred embryos to pseudopregnant recipients. Of the 225 embryos transferred, from a total of 3 pools of 3 males, 80 developed to term (35.6%). This is approximately a three to five fold enhancement over previous data obtained in Applicants' and many other IVF labs with cryopreserved C57BL/6 sperm (FIG. 4).

Example 8

Cryopreservation of Sperm from Genetically Modified Mice with CPM Containing MTG and Recovery to Live Born Ten μL aliquots of sperm from a variety of mouse strains as listed in Table 7 are frozen in the CPM with 477 μM monothioglycerol as ROS(CPM). A total of at least 6 sperm samples per treatment within a strain are utilized. These represented at least 3 samples from each of at least 2 sets of 2 males whose sperm are pooled at the time of collection and then split into the two treatments. Subsequent to thawing the samples are placed directly into their own 500 μL in vitro fertilization (IVF) drop of Cooks Mouse Vitro Fert (Cook Australia; Queensland, Australia; (Quinn et al., 1995)). After an hour incubation, 4 cumulus intact oocyte clutches from isogenic strains were added to the incubation medium. Following a 4 hr co-incubation, the presumptive zygotes were washed and cultured overnight. Approximately 18 hours later, the fertilization rate was determined (% 2 cell: #2-cell embryos/# total oocytes, see Table 7). The average percentage was determined. For each line, about 30 2-cell embryos were implanted into receptive females. After approximately 21 days, the number of live born mice was determined, shown as % Live born in Table 7.

In summary, the procedures described herein, in which cryoprotective media as described above was used, give good and consistent results for genetically modified mouse sperm, comparable to the parental inbred strains. With the parental strains, the following fertilization rates have been obtained: 129S1/SvImJ 18%; C57BL/6J 68%; Balb/cJ 58%, for BALB/cByJ 69%, and FVB/NJ 98%.

TABLE 7

| Sperm Donor | Oocyte Donor | # Oocytes | # 2-Cell Embryos | % 2-Cell Embryos | % Live Born |
|---|---|---|---|---|---|
| C57BL/6-Tg(Csf1r-EGFP-NGFR/FKBP1A/TNFRSF6)2Bck/J | C57BL/6J | 219 | 59 | 26.94 | 43.3 |
| B6(Cg)-Ncf1<m1J>/J | C57BL/6J | 218 | 84 | 38.53 | 43.3 |
| B6.Cg-Mapt<tm1(EGFP)Klt>Tg(MAPT)8cPdav/J | C57BL/6J | 224 | 54 | 24.11 | 30 |
| B6.129S-Shh<tm2(cre/ESR1)Cjt>/J | C57BL/6J | 182 | 142 | 78.02 | 26.7 |
| B6; C3H-Tg(Scgb1a1-Scnn1b)6608Bouc/J | B6C3FeF1 | 209 | 180 | 86.12 | 66.7 |
| CByJ.A-Ttc7<fsn>/J | BALB/cByJ | 221 | 176 | 79.64 | 46.7 |
| B6.129S2(C)-Stat6<tm1Gru>/J | C57BL/6J | 223 | 223 | 100 | 43.3 |
| C3.B6-Tg(Fabp1-Ccnd1)4Rdb/J | C3H/HeJ | 138 | 107 | 77.54 | 26.7 |
| B6.129S1-Csf2rb1<tm1Cgb>/J | C57BL/6J | 253 | 37 | 14.62 | 35.7 |
| B6.HRS(BKS)-Cpe<fat>/J | C57BL/6J | 237 | 116 | 48.95 | 13.3 |
| B6.D2N-Ahr<d>/J | C57BL/6J | 143 | 67 | 46.85 | 40 |
| B6.Cg-F2rl1<tm1Mslb>/J | C57BL/6J | 186 | 95 | 51.08 | 50 |
| B6.129P2-P2rx7<tm1Gab>/J | C57BL/6J | 242 | 79 | 32.64 | 50 |
| FVB-Tg(Sod1-G86R)M1Jwg/J | FVB/NJ | 134 | 40 | 29.85 | 48 |
| C.Cg-Fv4<r>/HmJ | BALB/cJ | 138 | 21 | 15.22 | 28.6 |
| C.Cg-Gata1<tm6Sho>/J | BALB/cJ | 70 | 61 | 87.14 | 20 |
| STOCK Dicer1<tm1Bdh>/J | C57BL/6J | 217 | 128 | 58.99 | 46.7 |
| B6.Cg-Gusb<mps>/BrkJ | C57BL/6J | 289 | 60 | 20.76 | 33.3 |
| B6.129S4-Cxcl10<tm1Adl>/J | C57BL/6J | 257 | 64 | 24.90 | 50 |
| B6.Cg-Msr1<tm1Csk>/J | C57BL/6J | 161 | 35 | 21.74 | 53.3 |
| B6; 129S7-Ephb4<tm1And>/J | C57BL/6J | 285 | 100 | 35.09 | 36.7 |
| B6.Cg-Tg(F2RL1)1Mslb/J | C57BL/6J | 235 | 113 | 48.09 | 33.3 |
| B6.129S2-Thbs1<tm1Hyn>/J | C57BL/6J | 204 | 62 | 30.39 | 56.7 |
| B6.Cg-Tg(PDGFB-APPSwlnd)20Lms/2J | C57BL/6J | 232 | 55 | 23.71 | 36.7 |
| B6.C3-Gusb<mps-2J>/BrkJ | C57BL/6J | 188 | 57 | 30.32 | 30 |
| B6.C-H2<bm1>/ByBir-Gusb<mps>/SopJ | B6.C-H2<bm1>/ByJ | 94 | 22 | 23.40 | 47.6 |
| B6.Cg-Tg(ACTB-EGFP)1Osb/LeySopJ | C57BL/6J | 299 | 116 | 38.80 | 36.7 |
| B6.129S6-Ppt1tm1Hof/J | C57BL/6J | 227 | 121 | 53.30 | 30 |
| C3H/HeOuJ-Gusb<mps-2J>/BrkJ | C3H/HeOuJ | 211 | 134 | 63.51 | 36.7 |
| C57BL/6J-Kit<W-41J>/SopJ | C57BL/6J | 304 | 109 | 35.86 | 53.3 |
| 129-Gt(ROSA)26Sor<tm1Luo>/J | 129/SvImJ | 281 | 85 | 30.25 | 30 |
| CBy.Cg-Gpi1<a-m1Ehs>/BrkJ | BALB/cJ | 141 | 25 | 17.73 | 58.3 |
| B6.Cg-Gpi1<a-m1Ehs>/BrkJ | C57BL/6J | 195 | 49 | 25.13 | 20 |

Example 9

Cryopreservation of Rat Sperm

The epididymides and vas deferentia were collected from one 33 week old LEW/SsNHsd rat (Harlan, Indianapolis, Ind.). Incisions were made in the tissue and the sperm were allowed to swim out, into 2 mL of a solution containing 8% lactose [w/v] (Sigma Aldrich; St. Louis, Mo.) and 23% egg yolk [v/v] from fresh eggs in distilled water (Invitrogen; Carlsbad, Calif.) for 10 min. The sperm suspension was then split with half being placed into the lactose/egg yolk solution and the other half being suspended in lactose/egg yolk solution containing 954 micromol MTG in 15 mL conical tubes. This resulted in a final MTG concentration of 477 µM. The 15 mL conical tubes containing the sperm samples were placed into a beaker containing ~150 mL of 15° C. water for 10 min. After the initial cooling period, the beaker containing the water and conical tubes was transferred to a 4° C. refrigerator where the samples were cooled for an hour and 15 min. After cooling to 4° C., the sperm was diluted into six different media compositions as described in Table 8. The CPM for rat sperm had the following composition: cryoprotectant was lactose alone or lactose and glycerol or propylene glycol; the membrane protectant was fresh chicken egg yolk and MTG as the free radical scavenger.

The sperm were loaded into 250 µL French straws (IMV; Maple Grove, Minn.; cat# AAA201), which were then sealed with an instantaneous heat sealer (model AIE-305HD; American International Electric; Whittier, Calif.) and 5 of them loaded into cassettes (Zanders Medical Supplies; Vero Beach, Fla.). The cassettes were placed onto a raft situated within a styrofoam box containing liquid nitrogen and the samples were exposed to $LN_2$ vapor for at least 10 min before being plunged into the liquid phase. The apparati employed essentially allowed the sperm to be cooled at 37° C./min from a temperature of −10° C. to a temperature of −60° C. Sperm samples were stored in liquid nitrogen for at least 20 hours. The samples were thawed in a 37° C. water bath and pushed out the straw into a 35×10 mm standard BD Falcon petri dish (Fisher Scientific, USA). The sperm were diluted 1:50 in Cooks Mouse Vitro Fert (Cook's; Spencer, Ind.) and motility was evaluated by counting at least 5 different fields using a video monitor connected to a microscope using a magnification of 40×. The following values were used: 0 for no motility, + to ++++ for the proportion of motile cells with ++++ being the highest. In all cases tested, the addition of MTG yielded an increased motility with the CPM composed of lactose, glycerol, egg yolk and MTG giving the best result.

TABLE 8

Analysis of Rat Sperm Motility After Cryopreservation in a Number of Different Media

| CPM composition | | | Motility Response |
|---|---|---|---|
| Cryo Protectant | Membrane Protectant | Free Radical Scavenger | After Thawing |
| 8% lactose | 23% egg yolk | | + |
| 8% lactose | 23% egg yolk | 477 µM MTG | + |
| 8% lactose, 0.9M glycerol | 23% egg yolk | | ++ |
| 8% lactose, 0.9M glycerol | 23% egg yolk | 477 µM MTG | ++++ |
| 8% lactose, 0.9M propylene glycol | 23% egg yolk | | 0 |

TABLE 8-continued

Analysis of Rat Sperm Motility After Cryopreservation in a Number of Different Media

| CPM composition | | | Motility Response |
|---|---|---|---|
| Cryo Protectant | Membrane Protectant | Free Radical Scavenger | After Thawing |
| 8% lactose, 0.9M propylene glycol | 23% egg yolk | 477 µM MTG | +++ |

Example 10

Cryopreservation of Bovine Sperm

Semen was collected via an artificial vagina from 6 different Holstein bulls over 3 different days. The bulls were selected such that three produce sperm with good consistent freezing quality and three produce sperm that respond to cryopreservation with poorer consistency. Antibiotics were added to the neat semen and initial volume and concentration were determined using a graduated cylinder and spectrophotometry. From each collection, 5 different 500 µL aliquots of semen were extended with 1.5 mL of Triladyl egg yolk extender (Minitube; Verona, Wis.) containing glycerol. Subsequently, 2 mL of the same extender containing no MTG, 200, 1000, 2000 or 10,000 µM MTG was added to the extended semen to yield the final concentrations for MTG of 0, 100, 500, 1000 or 5000 µM. After extension, the semen was transferred to a cold room and cooled to 4° C. over ~1.5 hours. Extender containing the appropriate 1× concentration of MTG was supplied to each aliquot bringing the final sperm concentration to $80 \times 10^6$/mL. This extended plus semen was loaded into ¼CC French Straws using automated fillers (MRS4; IMV technologies, Maple Grove, Minn.) and stored at 4° C. for 3 hrs. Following the equilibration time period, the straws were frozen in a controlled rate freezer as follows: 4° C./min to −12° C.; 40° C./min to −100° C.; 20° C./min to −140° C. The samples were transferred to goblets and stored in liquid nitrogen until examination.

For the examination, 6 straws per treatment per collection were thawed in a 37° C. water bath for at least 60 sec. For each treatment within a collection, two pools of semen were created and analyzed by combining the contents of three straws. For motility, the sperm samples were diluted 1:3 in phosphate buffered saline (PBS) and stained with 100 µg/mL of the fluorescent DNA stain Hoechst 33342 before they were examined using the Hamilton Thorne Integrated Visual Optics System (IVOS). The percent of motile sperm was determined on 4 different fields within each of 2 separate chambers. For viability the sperm samples were diluted 1:100 in PBS and stained with SYBR 14 (00 nM) and propidium iodide (12 µM About 10,000 cells were counted using the Partec Flomax Flow Cytometer (Ft. Collins, Colo.).

Results:

Motility. No differences were detected in motility among the treatments. This non-discrepancy was maintained even after 3 hr of incubation. Similarly, when bulls were grouped based on their sperm freezability characteristics, no differences at 0 or 3 hrs were detected. These results show that the CPM consisting of glycerol, egg yolk and MTG at various concentrations has no ill effects on the overall post-thaw motility of bull sperm.

Figure 5A:
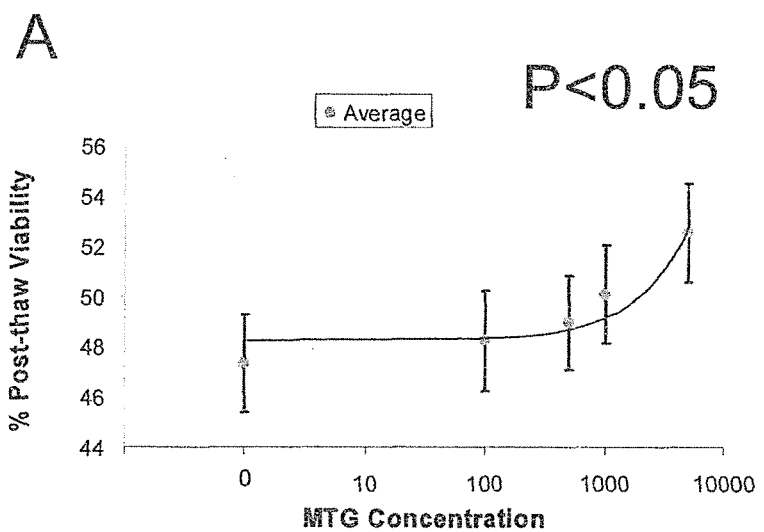
FIGS. 5A-5G demonstrate that the presence of monothioglycerol (MTG) during bovine sperm cryopreservation enhances post-thaw viability. Sperm from three collections from each of 6 different bulls were frozen in the presence of MTG at the concentrations indicated on the x-axes. For each collection, two sets of three straws each were created and analyzed twice for sperm viability. Differences in sperm cell viability among the treatments were determined using analysis of variance on arcsine transformed percents and pre-planned comparisons to the control of no MTG using Dunnett's method. Panel A illustrates the mean and standard errors for the 6 bulls while panels B though G illustrate the percent of viable sperm for the individuals. An overall treatment affect was noted as were differences within those bulls shown in panels B, C, and D.
Figure 5B:
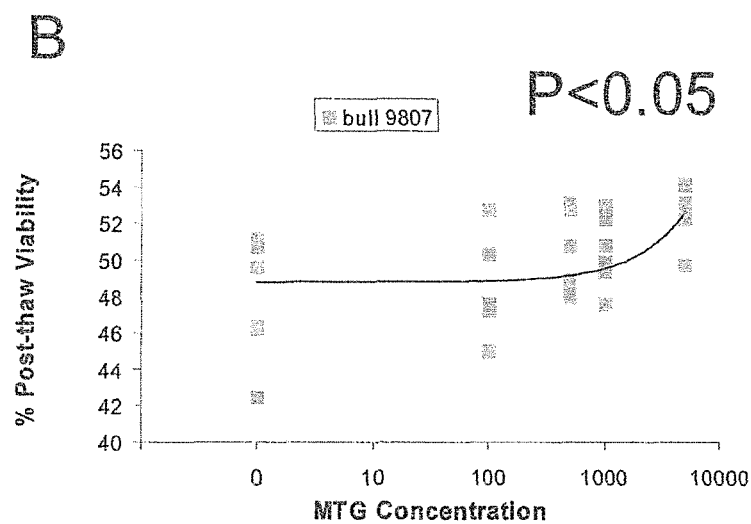
Figure 5C:
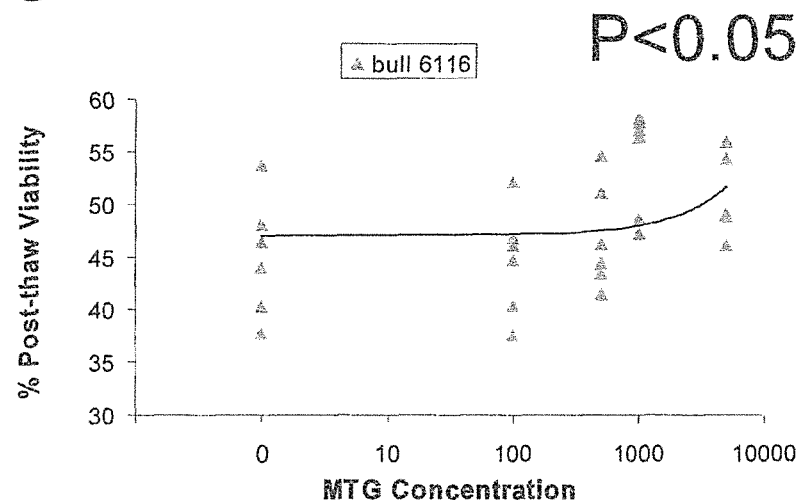
Figure 5D:
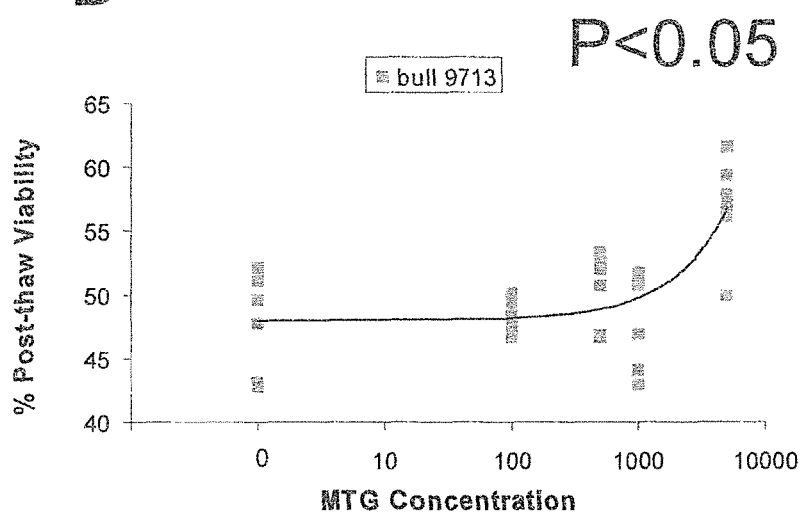
Figure 5E:
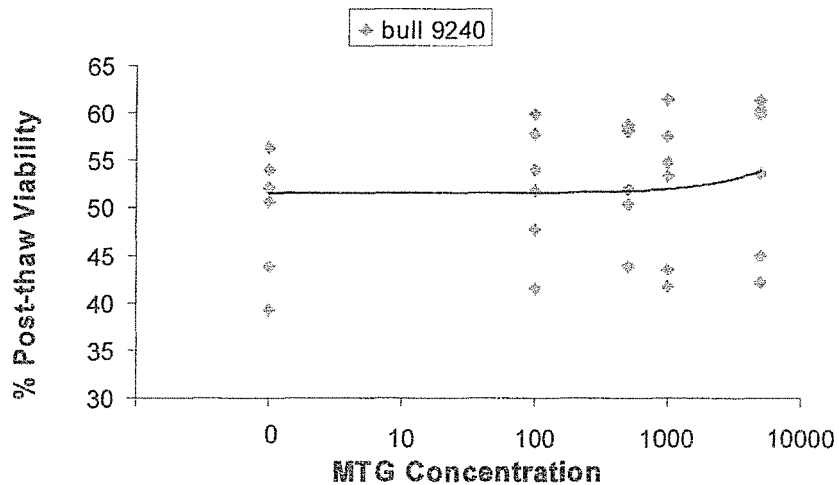
Figure 5F:
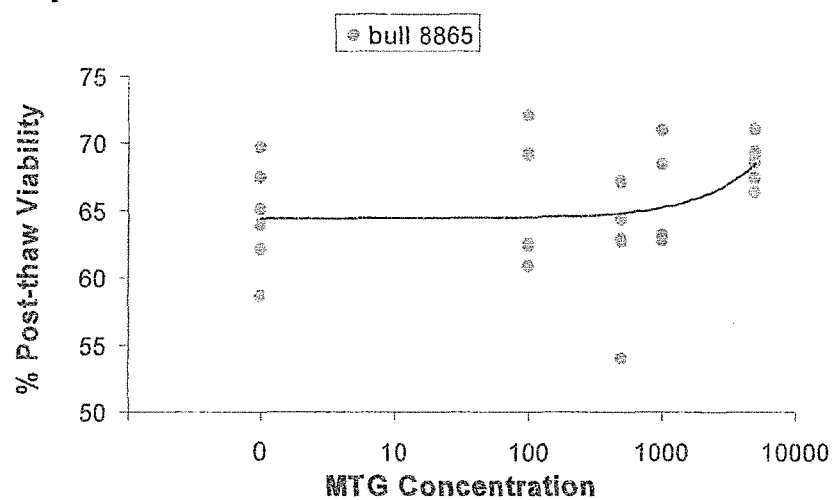
Figure 5G:
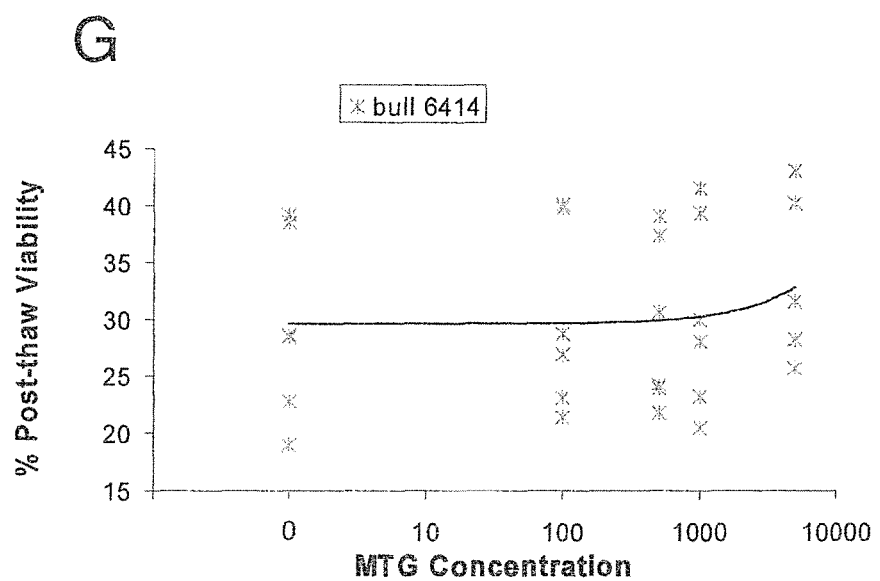

Viability. As shown in FIG. 5C, the overall viability was not negatively influenced by the CPM consisting of glycerol, egg yolk and MTG at various concentrations. When individual bulls were analyzed individually (FIG. 5C) positive effects appear evident.

Addition of MTG to the cryopreservative media results in increase of viability with a slight effect for the 3 bulls and about an 8% increase for the other 3 bulls.

Example 11

Human Semen Cryopreservation

One semen sample is collected from each of healthy, normal, fertile males. Fertile men are defined as individuals aged 19-30 who have naturally fathered a child within the past 6 months. Furthermore, the samples are considered normal if they meet the parameters set by WHO criteria for sperm count, motility, and morphology. The semen sample is collected after a minimum of 48-72 hours of sexual abstinence, but not longer than seven days. The semen is obtained by masturbation and ejaculated into a sterile, wide-mouthed plastic container that has been toxicity tested. The subject is instructed that care must be taken to include the entire specimen in the container. Upon receipt of the ejaculate by the laboratory, each semen sample is entered in a semen analysis logbook. The semen sample is assigned a consecutive accession code number, which is recorded along with the patient's name and the date of collection. The patient's sample is identified by the accession code number throughout the freezing procedure; all tubes, slides, etc. are labeled with this number. While the sample liquefies, the cryoprotective media is freshly prepared: TYB (Irvine Scientific, cat. #90128: 20% egg yolk—from USDA certified SPF (Virus Free) laying flocks, heat inactivated at 56° C. for 30 minutes; 12% v/v Glycerol; 10 μg/mL Gentamicin Sulfate) and 477 μM MTG or TYB alone. For control TYB media without MTG is used.

The semen sample is gently mixed with the freshly prepared cryoprotective media at a 1:1 ratio and 0.25 mL volumes of the sample/cryoprotectant mixture is transferred into each of the labeled cryovial (1 ml from Nunc). The cryovials are placed into a metal rack and is suspended in the $LN_2$ vapors of the storage tank for 12 minutes. After 12 minutes, the cryovials are placed onto the labeled, chilled aluminum cane, and the cane is inserted into the labeled, chilled cardboard sleeve and plunged into a canister in the storage tank. The cryopreserved semen will be stored for at least 1 hour in the liquid nitrogen. A single vial will be thawed by placing the cryovial into a beaker containing 37° C. warm water for 10 minutes. Then the sample is gently mixed using a sterile pipette. The semen is analyzed for morphology (e.g. acrosome), motility, progression, viability, and count immediately after thawing. The zona free hamster oocyte penetration test or the chlorotetracycline capacitation assay can be performed to determine the quality of the semen.

Example 12

Preparation and Storage of Cryoprotective Media

Approximately 80 mL of bottled distilled water (Invitrogen, cat #15230-238) was placed in a beaker and heated for 40 sec in a microwave on high power. Care was taken not to boil. The beaker was placed on a heated stir plate and 18 g of raffinose (Sigma; cat #R7630) was added. The solution was heated and stirred until it cleared. Subsequently, 3 g of skim milk (BD Diagnostics; cat #232100) was added and the solution was stirred until the skim milk powder dissolved. The solution was transferred to a volumetric flask and brought to 100 mL with sterile distilled water (Invitrogen, cat #15230-238). Again, the solution was mixed well and divided into two 50 mL centrifuge tubes. To clarify the solution, it was centrifuged at 13,000×g for 15 minutes at room temperature (22° C.) and then filtered through a 0.22 μm cellulose filter. This resulted in an 18% raffinose/3% skim milk solution having a final osmolarity of 488 mOsm. One third of this solution was supplemented with 477 μM monothioglycerol (MTG; Sigma cat M6145) and frozen at −80° C. in an Elite® Series Revco Freezer (Asheville, N.C.). The other two thirds were frozen at −80° C. without any supplementation.

After 8 weeks of storage at −80° C., the raffinose skim milk solutions were thawed in a 37° C. water bath until no more precipitate was observed (~1 hr). The first cryoprotective media consisted of 18% raffinose, 3% skim milk, 477 μM MTG frozen for 8 weeks (FROZEN MTG). The second cryoprotective media consisted of 18% raffinose and 3% skim milk frozen for 8 weeks being supplemented at the time of sperm collection with 477 μM fresh MTG (FRESH MTG). The third cryoprotective media consisted of 18% raffinose and 3% skim milk which had been frozen at −80° C. for 8 weeks (NO MTG).

Eighteen C57BL/6J males were sacrificed and their vas deferentia and epididymides were obtained and sperm was isolated as previously described (see Example 1). Nine different groups, of two males each, were created and each group was assigned to have their sperm collected into one of three different cryoprotective media. This resulted in 3 groups of males being collected for each treatment. Four aliquots, of 10 μl each, were loaded into ten ¼ CC French straws (IMV; Maple Grove, Minn.; cat# AAA201). These were then sealed with an instantaneous heat sealer (model AIE-305HD; American International Electric; Whittier, Calif.) and 5 of them loaded into a cassette (Zanders Medical Supplies; Vero Beach, Fla.). The cassettes were placed onto a raft situated within a Styrofoam box containing liquid nitrogen and the samples were exposed to $LN_2$ vapor for at least 10 min before being plunged into the liquid phase. This allowed the sperm to be cooled at 37° C./min from a temperature of −10° C. to a temperature of −60° C. The sperm samples were stored in liquid nitrogen for approximately 3 months.

To determine if storage of the cryoprotective media at −80° C. altered the activity of the C57BL/6J mouse sperm, in vitro fertilizations (IVF) were preformed as described previously (see Example 1, also see publications by Nakagata, 2000a; Nakagata, 2000b, Sztein et al. 2000; Byers et al. 2006). Briefly the sperm and oocytes, both from C57BL/6J mice, were incubated together for 4 hrs in a benchtop incubator at 37° C. After 4 hrs of co-incubation the presumptive zygotes were washed through two 150 μL drops of IVF media (MVP; Cook's; Spencer, Ind.) and then cultured overnight. Approximately 18 hrs later, the proportion of oocytes fertilized was calculated by dividing the number of two-cell embryos by the sum of two-cells and normally appearing presumptive one-cell oocytes.

Figure 6:
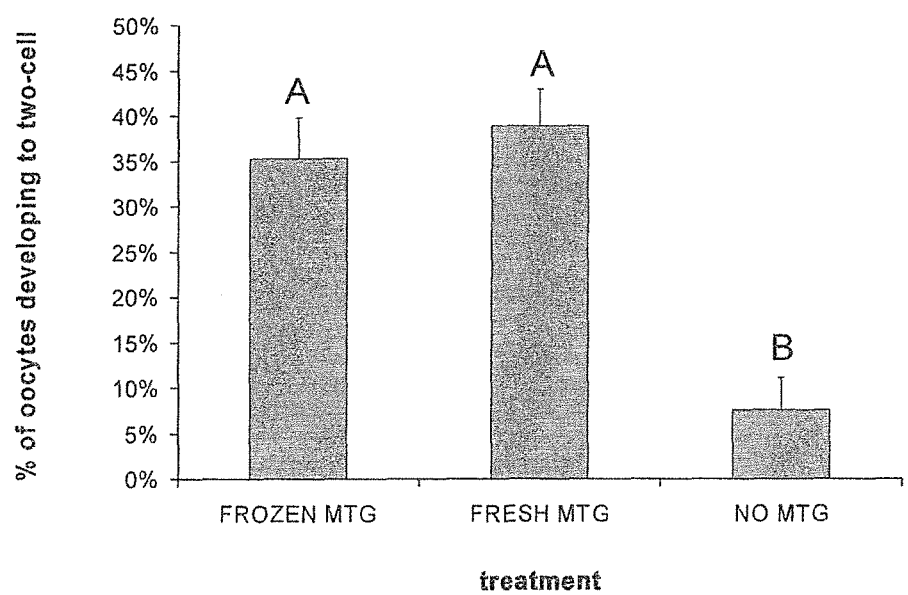
FIG. 6 compares frozen versus fresh monothioglycerol and its effects on fertilization rate.

FIG. 6 clearly demonstrates that storing the cryoprotective media with MTG for 2 months at −80° C. performs equally compared to cryoprotective media with freshly added MTG. The column FROZEN MTG shows the fertilization rate when C57BL/6J sperm was cryopreserved with the complete media being stored at −80° C. The column FRESH MTG shows the fertilization rate when C57BL/6J sperm was cryopreserved with media being stored at −80° C., but MTG being freshly added. The column NO MTG shows the fertilization rate when C57BL/6J sperm was cryopreserved with media being stored at −80° C., but not containing MTG freshly. Differences in the percent of oocytes developing to 2-cell among the treatments were determined using analysis of variance on arcsine transformed percents and comparisons for all pairs of means using Tukey-Kramer HSD (JMP; SAS Institute, Cary, N.C.) statistical analysis. Those means with different letters are significantly different (p<0.05). For presentation, the average and standard deviations of the percents are shown. No significant difference between the two media preparations FROZEN MTG and FRESH MTG can be observed.

Example 13

Identification of a Suitable Free Radical Scavenger

A suitable free radical scavenger (useful for cryopreservation of sperm) can be identified by testing one or more of the following activities (a) capability to reduce Reactive Oxygen Species (ROS), (b) effect on sperm motility, and (c) effect on in vitro fertilization (IVF). In those instances in which a suitable free radical scavenger for use with mouse sperm is being identified, (a) and (c) are assessed/carried out. For bovine sperm, (a) and (b) are carried out. In each instance, the third activity ((b) for mouse and (c) for bovine) can be carried out. In specific embodiments, one of either (b) or (c) above will be tested, in addition to (a) above.

For example, the capability to reduce ROS can be tested by a dye/sperm method as described in Example 4 and also see publications by Nelid et al 2006 and Guthrie and Welch 2006. Either fresh or cryopreserved sperm can be used in this assay. For example, sperm collected from the vas deferens and epididymis of two C57BL/6J mice into 1 mL of a solution containing 3% skim milk (w/v; BD Diagnostics; cat #232100) and 18% raffinose (w/v; Sigma; cat #R7630). A fraction of the collected sperm was diluted 1:1 in the same skim milk raffinose solution while another fraction was diluted 1:1 using the skim milk raffinose solution supplemented with 954 mM monothioglycerol (MTG; Sigma Aldrich; cat #M6145). Another set of C57BL/6J males was used to collect sperm and dilute in the skim milk raffinose solution with 1 mM glutathione (GSH; Sigma Aldrich; cat #G6013) or 2 mM dithiothreitol (DTT; Sigma Aldrich; cat #646563). The sperm was cryopreserved as described in Example 1 and stored in liquid nitrogen for at least 24 hours.

Figure 7A:
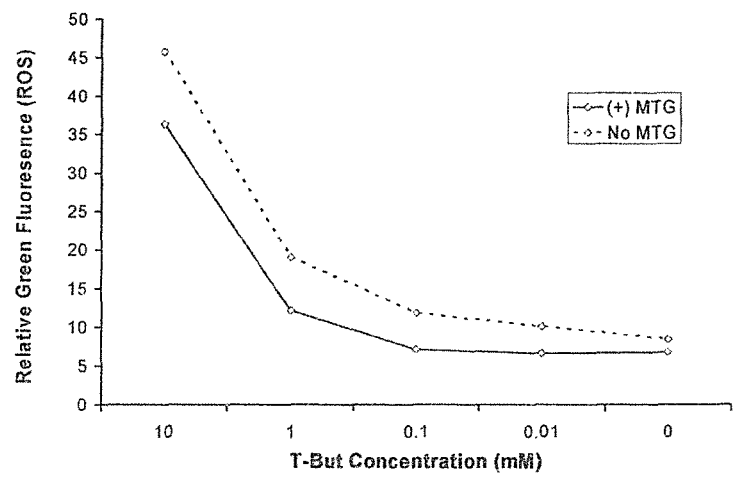
FIGS. 7A and 7B show results of assessments carried out to identify suitable free radical scavengers.
Figure 7B:
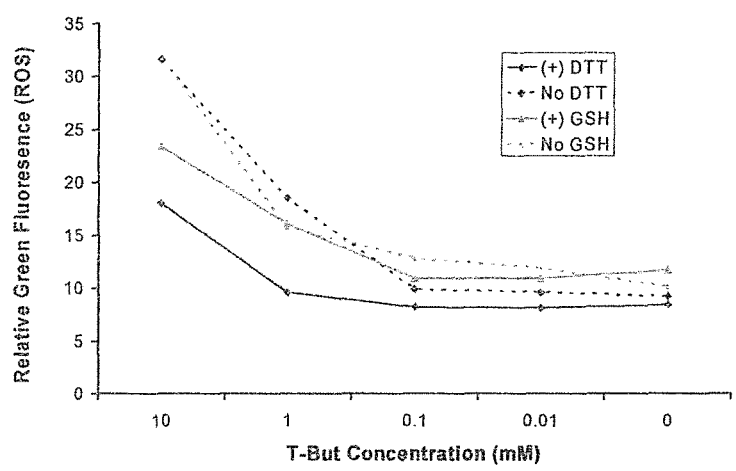
Figure 8:
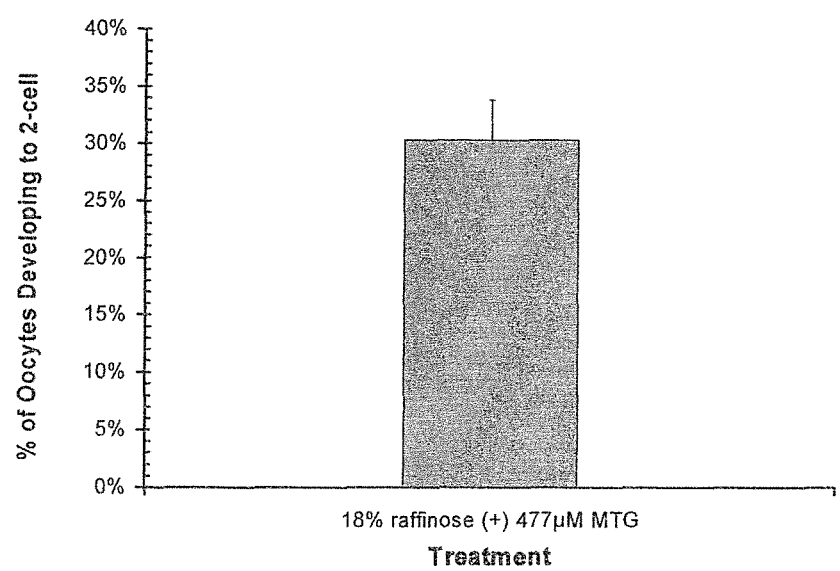
FIG. 8 shows results of work in which sperm from C57BL/6J were frozen in 18% Raffinose supplemented with 477 µM monothioglycerol. The sperm were thawed and used for in vitro fertilization using oocytes from superovulated C57BL/6J females. With this approach viable sperm were obtained and fertilized 30% of the oocytes.

To determine if MTG, GSH or DTT can act as a free radical scavenger, the sperm were thawed and loaded with the green fluorescent dye 5-(and-6)-chloromethyl-2',7'-dichlorodihydrofluorescein diacetate (CM-H2DCFDA; Invitrogen C6827). This dye is a cell-permeant indicator for reactive oxygen species that is nonfluorescent until removal of the acetate groups by intracellular esterases and oxidation occurs within the cell. The emission of fluorescence correlates with ROS generation as a result of DCFH oxidation. To load the sperm, at least 150 µL of sperm were thawed and diluted 1:1 in a sperm incubation media described by Bath et al. ((Bath 2003); 123 mM NaCl; 4.7 mM KCl; 0.2 mM $MgSO_4.7H_2O$; 10 mM; $NaHCO_3$ 21 mM HEPES; 0.33 mM sodium pyruvate; 4.6 mM glucose; 100 IU/mL penicillin G; 1.33 mg/mL BSA). The lyophilized dye was resuspended in dimethylsulfoxide to a concentration of 432.5 µM and then added to the cells, such that the final dye concentration was 40 µM. The sperm were allowed to take up the stain for 30 min and then 50 µL of the cells was aliquoted into Fluorescent-activated cell sorting (FACS) tubes (12×75 mm tubes polystyrene, Falcon #2052 or 2054 or polypropylene tubes, USA Plastics PN 1450-0000). Five hundred microliters of sperm incubation media containing a 50 fold dilution of the potential reducing agent used to cryopreserve sperm was added. This level of reducing agent was selected to reflect the same 50 fold dilution observed during a routine in vitro fertilization. Then the sperm were centrifuged for 5 min at 300×g, the supernatant was decanted and the cells were resuspended in 100 µL of sperm incubation media containing the 50 fold dilution of the appropriate potential reducing agent. The sperm were then challenged with various concentrations of tert-Butyl hydroperoxide (e.g. Sigma Aldrich; cat #B2633) to induce oxidative stress. The stressed samples were incubated for 1 hour, brought to 300 µL in sperm incubation media supplemented with the reducing agent being investigated and then stained with 5 µg/mL of propidium iodide (e.g. Invitrogen, cat #P-3566) and 5 µg/mL of LDS-751 (Invitrogen, cat #L7595) to differentiate nucleated live and dead cells. The samples were loaded onto either a FACScan (BD Biosciences; Franklin Lakes, N.J.) or FACSCalibur (BD Biosciences; Franklin Lakes, N.J.) flow cytometer and the green fluorescence was measured on at about 5,000 viable sperm. FIGS. 7A and 7B show that all of the additives tested in this experiment reduced the level of reactive oxygen species within cryopreserved mouse sperm cells.

FIGS. 7A and 7B show results of the following: C57BL/6 sperm cryopreserved in the presence and absence of three potential free radical scavengers (monothioglycerol (MTG); dithiothreitol (DTT); glutathione (GSH)) were loaded with the green fluorescent dye CM-H2DCFDA to measure intracellular reactive oxygen species (ROS). The sperm were challenged with varying levels of tert-butyl hydroperoxide to induce oxidative stress and green fluorescence was measured using flow cytometry (A) FACSCalibur and (B) FACScan. As shown, the potential reducing agents limited the level of ROS within the cryopreserved mouse sperm. The y-axis shows the relative fluorescence being the highest when no free radical scavenger is present (solid line) and the x-axis shows the concentration of tert-butyl hydroperoxide.

If the compound is capable of reducing ROS at the tested concentration, then its effect on sperm motility and fertilization is tested. While the sperm motility assay is a helpful fast screening tool in the case of mouse, this assay is not required for mouse and one can perform only the IVF assay in the case of mouse. For other species, e.g. bovine, the sperm motility assay together with the fluorescence assay is sufficient. The sperm motility assay can be done either with fresh or cryopreserved sperm. For example, the motility can be determined as described in Example 6 (Determination of Sperm Concentration and Motility), using an IVOS instrument. Briefly, C57BL/6 sperm were diluted 1:50 in pre-warmed and gassed mouse vitro fert (Cook's; Spencer, Ind.) under light mineral oil. The samples were incubated for an hour at 37° C., in a humidified atmosphere of 5% $CO_2$, 5% $O_2$ and 90% nitrogen in a K-MINC-1000 bench top incubator (Cook's; Spencer, Ind.). After incubation, the sperm were drawn into 0.1×2.0 mm I.D. tubes (VitroCom Inc. Mt Lks. N.J.) using capillary action and 3 manually selected fields per sample were analyzed for motility using the Hamilton Thorn (Beverly, Mass.) integrated visual optics system (IVOS) for computerized semen analysis. Applicants have shown that sperm frozen in CPM containing no free radical scavenger, 0.477 mM MTG, 0.1 mM DTT, 1 mM DTT, 5 mM DTT, 20 mM DTT, 0.5 mM GSH, 1 mM GSH, 5 mM GSH or 50 mM GSH can be assessed for motility and that motility of at least 5% is required to achieve fertilization in IVF. All measurements were done in triplicate and the average is listed in Table 9.

TABLE 9

C57BL/6 Sperm Motility after Different CPM Treatments

| Free Radical Scavenger | Average Post Thaw Motility | IVF Fit |
|---|---|---|
| none | 10-29% | yes |
| 0.1 mM DTT | 24.6% | yes |
| 1 mM DTT | 34% | yes |
| 5 mM DTT | 17.6% | yes |
| 20 mM DTT | 1.6% | no |
| 0.5 mM GSH | 32% | yes |
| 1 mM GSH | 25.3% | yes |
| 5 mM GSH | 41.67% | yes |
| 50 mM GSH | 0.6% | no |
| 0.477 mM MTG | 16% | yes |

If the compound has passed the sperm/dye test and the motility test, then its effect on IVF is tested. IVF was performed, as described in Example 1, with C57BL/6 sperm cryopreserved in the media containing as free radical scavenger, DTT, GSH or MTG.

TABLE 10

C57BL/6 Sperm Fertility After Different CPM Treatments

| Free Radical Scavenger | Fertilization Rate (2-cell embryos of total oocytes) |
|---|---|
| None | 31.2% (56 of 179) |
| 0.1 mM DTT | 19.2% (33 of 169) |
| 1 mM DTT | 2% (2 of 94) |
| 5 mM DTT | 0.9% (2 of 212) |
| 20 mM DTT | 6.4% (11 of 147) |
| 0.5 mM GSH | 59.7% (138 of 229) |
| 1 mM GSH | 49.5% (99 of 202) |
| 5 mM GSH | 39.9% (74 of 195) |
| 50 mM GSH | 0.0% (0 of 249) |
| 0.477 mM MTG | 75.2% (111 of 149) |

These data clearly show that sperm with a motility below 5% are compromised and have less ability to fertilize oocytes (20 mM DTT and 50 mM GSH). Further, these data show that, in addition to the motile sperm criteria, the fertilization rate results in a reliable assay to determine the effectiveness of compound and its dose.

Example 14

Cryopreservation of Mouse Spermatozoa with CPM Containing a Cryoprotectant and a Free Radical Scavenger (CP-FRS)

The epididymides and vas deferentia are extracted from three C57BL/6J males and placed into the cryoprotective media described herein. Sperm are extracted and placed into an incubated 1 mL collection drop of CryoProtective Medium (CPM), which comprises, for example, raffinose [18% w/v] and monothioglycerol [MTG: 100 µM to 1 mM] or raffinose [18% w/v] and reduced glutathione [GSH; 500 µM to 50 mM]). In this example, Applicants used 18% w/v raffinose and 477 µM monothioglycerol. The sperm were allowed to swim out into the CPM; this was allowed for at least 5 minutes, but for less than 20 min. The residual tissues were then removed from the collection drop. Ten microliters of the sperm sample were loaded into as many as one hundred 250 µL French straws (IMV; Maple Grove, Minn.). Four 10 µl aliquots of the collected sperm were loaded into the straws, which were sealed with an instantaneous heat sealer. The straws were placed into cassettes and exposed to liquid nitrogen vapor for 10 minutes. This essentially cooled the sperm at 37° C./min. After being stored in liquid nitrogen for at least 24 hours, 6 samples from each treatment were thawed in a 37° C. water bath for 30 sec, and then each 10 µL aliquot was placed directly into its own 500 µl in vitro fertilization (IVF) drop of Cooks Mouse Vitro Fert (Cook Australia; Queensland, Australia: Quinn et al., 1995). After an hour of incubation, 4 cumulus intact oocyte clutches from superovulated C57BL/6J females were added to the in vitro fertilization drop (see Example 1 and also Nakagata, 2000a; Nakagata, 2000b, Sztein et al. 2000; Byers et al. 2006).

Briefly, the sperm and oocytes, both from C57BL/6J mice, were incubated together for 4 hrs in a benchtop incubator at 37° C. After 4 hrs of co-incubation the presumptive zygotes were washed through two 150 µL drops of IVF media (MVF; Cook's; Spencer, Ind.) and then cultured overnight. Approximately 18 hrs later, the proportion of oocytes fertilized was calculated by dividing the number of two-cell embryos by the sum of two-cells and normally appearing presumptive one-cell oocytes.

TABLE 1

Animals for Which the Present Invention Can be Used

| Category | Examples but not limited to: | Notes: |
|---|---|---|
| INBRED MOUSE LINES | C3H<br>CBA<br>DBA<br>FVB<br>NOD<br>BALB/c<br>129<br>C57BL | |
| C57BL Mice | C57BL/6J, C57BL/6NTac, C57BL/6NCrl, C57BL/10 | Definition: Inbred Mice are genetically homogeneous and homozygous at all loci. The International Committee on Standardized Nomenclature for Mice has ruled that a strain of mice can be considered "inbred" at generation $F_{20}$ |
| All other inbred mouse strains, including recombinant inbred strains | 129S1/SvImJ, 129T2/SvEmsJ, 129X1/SvJ, 129P3/J, A/J, AKR/J, BALB/cBy, BALB/cByJ, BALB/c BALB/cJ, C3H/HeJ, C3H/HeOuJ, C3HeB/FeJ, C57BL/10J, C58, CBA/CaHN-Btkxid/J, CBA/J, DBA/1J, DBA/1LacJ, DBA/2J, FVB/NJ, MRL/MpJ, NOD/LtJ, SJL/J, SWR/J, NOR/LtJ, NZB/BINJ, NZW/LacJ, RBF/DnJ, 129S6/SvEvTac, AJTAC, BALB/cAnNTac, BALB/cJBomTac, | |

TABLE 1-continued

Animals for Which the Present Invention Can be Used

| Category | Examples but not limited to: | Notes: |
|---|---|---|
| | BALB/cABomTac, C57BL/6NTac, C57BL/6JBomTac, C57BL/10SgAiTac, C3H/HeNTac, CBA/JBomTac, DBA/1JBomTac, DBA/2NTac, DBA/2JBomTac, FVB/NTac, NOD/MrkTac, NZM/AegTac, SJL/JcrNTac, BALB/cAnNCrlBR, C3H/HeNCrlBR, C57BL/6NCrlBR, DBA/2NCrlBR, FVB/NCrlBR, C.B-17/lcrCrlBR, 129/SvPaslcoCrlBR, SJL/JorllcoCrlBR, A/JolaHsd, BALB/cAnNHsd, C3H/HeNHsd, C57BL/10ScNHsd, C57BL/6NHsd, CBA/JCrHsd, DBA/2NHsd, FVB/NHsd, SAMP1/KaHsd, SAMP6/TaHsd, SAMP8/TaHsd, SAMP10/TaHsd, SJL/JCrHsd, AKR/OlaHsd, BiozziABH/RijHsd, C57BL/6JOlaHsd, FVB/NhanHsd, MRL/MpOlaHsd, NZB/OlaHsd, NZW/OlaHsd, SWR/OlaHsd, 129P2/OlaHsd, and 129S2/SvHsd.<br>B6.129P2-Apoetm1Unc/J<br>NOD.CB17-Prkdcscid/J<br>129S1/SvImJ<br>129X1/SvJ<br>B10.A-H2a H2-T18a/SgSnJ<br>B10.D2-Hc0 H2d H2-T18c/oSnJ<br>B10.D2-Hc1 H2d H2-T18c/nSnJ<br>B10.RIII-H2r H2-T18b/(71NS)SnJ<br>B6(C)-H2-Ab1bm12/KhEgJ<br>B6.129P2-Il10tm1Cgn/J<br>B6.129P2-Nos2tm1Lau/J<br>B6.129P2-Nos3tm1Unc/J<br>B6.129S2-Cd8atm1Mak/J<br>B6.129S2-Igh-6tm1Cgn/J<br>B6.129S7-Ifngtm1Ts/J<br>B6.129S7-Rag1tm1Mom/J<br>B6.CB17-Prkdcscid/SzJ<br>B6.MRL-Faslpr/J<br>B6.V-Lepob/J<br>BKS.Cg-m +/+ Leprdb/J<br>C3HeB/FeJ<br>C57BL/10J<br>C57BL/10SnJ<br>C57BL/6-Tg(APOA1)1Rub/J<br>C57BL/6J-Tyrc-2J/J<br>CBA/CaHN-Btkxid/J<br>CBA/CaJ<br>CBySmn.CB17-Prkdcscid/J<br>FVB/N-Tg(MMTVneu)202Mul/J<br>KK.Cg-Ay/J<br>MRL/MpJ<br>MRL/MpJ-Faslpr/J<br>SJL/J<br>SWR/J<br>B10.PL-H2u H2-T18a/(73NS)SnJ<br>NONcNZO5/LtJ<br>WR<br>BPH/2<br>BPL/1<br>FS<br>P/J<br>P/A<br>PRO | |

TABLE 1-continued

Animals for Which the Present Invention Can be Used

| Category | Examples but not limited to: | Notes: |
|---|---|---|
| All genetically engineered (e.g. transgenic, knockout, knockin, knockdown, retroviral, viral), chemically induced mutations (e.g. ENU, EMS also including archives of mutants); radiation induced mutations; spontaneous mutations/modifications maintained on mouse strains for example: C57BL/6, 129, FVB, C3H, NOD, DBA/2, BALB/c, CD-1. Including congenic strains and recombinant congenic strains. | Examples: B6.129P2-Apoetm1Unc/J, B6.129S4-Pdyn$^{tm1Ute}$/J, B6; 129P2-Pemt$^{tm1J}$/J, NOD.Cg Prkdc$^{scid}$-B2m$^b$/Dvs, | |
| Mouse hybrid strains produced by crossing two inbred strains including mixed inbred strains | Mice:<br>NZBWF1/J<br>B6CBAF1/J<br>B6SJLF1/J<br>CB6F1/J<br>CByB6F1/J<br>PLSJLF1/J<br>WBB6F1/J-KitW/KitW-v<br>B6129PF1/J<br>CAF1/J<br>B6129PF2/J<br>B6129SF1/J<br>B6129SF2/J<br>B6AF1/J<br>B6C3F1/J<br>B6CBAF1/J<br>B6SJLF1/J<br>(including any other combination) Proportions vary from 50:50 F1 to 99:1 | |
| Outbred Mice | CD-1; ICR; Black Swiss; Swiss Webster; NIH Swiss; CF-1, Nude | Definition outbred: Animals from a defined population that are produced by breeding schemes that avoid crosses between closely related individuals in order to maintain the maximal level of heterozygosity in all offspring |
| INBRED RAT LINES | ACI, Brown Norway (BN), BCIX, Copenhagen (COP), MWF, D Agouti (DA), Goto-Kakizaki (GK), Lewis, Fischer 344 (F344), Wistar Furth (WF), Wistar Kyoto (WKY; WKYN1), ZDF F344/NTac-Tg(HLA-B27)-Tg(2M)33-3Trg; HsdAmc: TR-Abcc2; HsdHlr: ZUCKER-Leprfa; NIH Nude | |
| All genetically engineered (e.g. transgenic, knockout, knockin, knockdown, retroviral, viral), chemically induced mutations (e.g. ENU, also including archives of mutants); radiation-induced mutations; spontaneous mutations/modifications maintained on rat strains including congenic strains. | | |
| Rat Hybrids Produced by crossing two inbred strains | BHR<br>FBNF1/Hsd<br>LBNF1/Hsd | |
| Outbred Rats | Holtzman, Sprague Dawley, Long Evans, Wistar, Wistar Han, WH, WKY, Zucker, JCR (Russel Rat), OFA | Definition outbred: Animals from a defined population that are produced by breeding schemes that avoid crosses between closely related individuals in order to maintain the maximal level of heterozygosity in all offspring |
| All genetically engineered (e.g. transgenic, knockout, knockin, knockdown, retroviral, viral), chemically induced mutations (e.g. ENU, also including archives of mutants); radiation induced mutations; spontaneous mutations/modifications maintained on mammals | Rabbit, goat, sheep, pig, cow, horse, dog, cat | |

TABLE 1-continued

Animals for Which the Present Invention Can be Used

| Category | Examples but not limited to: | Notes: |
|---|---|---|
| Other rodents | Gerbils, Guinea pigs, Hamsters, Cotton Rat | |
| All genetically engineered (e.g. transgenic, knockout, knockin, knockdown, retroviral, viral), chemically induced mutations (e.g. ENU, also including archives of mutants); radiation induced mutations; spontaneous mutations/modifications maintained on vertebrates | Fish (e.g. zebrafish, medaka, salmon, tilapia, catfish, tuna); chicken, turkey | |
| Cows | as outbred or random bred populations | |
| Pigs | as outbred or random bred populations | |
| Goat | as outbred or random bred populations | |
| Sheep | as outbred or random bred populations | |
| Horses | as outbred or random bred populations | |
| Humans | as outbred or random bred populations | |
| All other mammals | Dogs, Cats, Camelids, Non-Human Primates, all outbred or random bred populations, zoo animals, marsupials, endangered mammals | |
| Other vertebrates | Freshwater fish (e.g. cyprinids, siluroids, salmonids, tilapia, medaka, zebrafish) Marine fish (e.g. herring, eel, sea bass, flounder, grouper, grunt, seatrout, drums, croaker, weakfish, dolphin, mackerels, tunas, snappers, swordfish, grouper, bluefish, bonefish, billfishes, tarpons, porgy, mullets, sharks, tarpons, tropical fishes); Endangered fish Birds (rooster, turkey, duck, goose, quail, pheasant, guinea fowl, pigeon, companion birds, endangered birds | |

REFERENCES

BATH, "Simple and efficient in vitro fertilization with cryopreserved C57BL/6J mouse sperm," (2003), Biol Reprod 68(1): 19-23.

GLENISTER, et al., "Cryoconservation—Archiving for the future," (2000), Mammalian Genome 11, 565-571.

NAKAGATA, "Cryopreservation of mouse spermatozoa," (2000a), Mammalian Genome 11, 572-576.

NAKAGATA, "Mouse Spermatozoa Cryopreservation," (2000b), J Mamm Ova Res 17, 1-8.

NAKAGATA, et al., "Cryopreservation of mouse spermatozoa from inbred and F1 hybrid strains," (1993), Jikken dobutsu Experimental animals 42, 317-320.

QUINN, P., et al., "Enhanced results in mouse and human embryo culture using a modified human tubal fluid medium lacking glucose and phosphate" (1995).

The antioxidant action of synthetic oestrogens involves decreased membrane fluidity: relevance to their potential use as anticancer and cardioprotective agents compared to tamoxifen? J Assist Reprod Genet 12, 97-105.

SONGSASEN, et al., "Cryopreservation of Mouse Spermatozoa II. Relationship between Survival after Cryopreservation and Osmotic Tolerance of Spermatozoa from Three Strains of Mice," (1997), Cryobiology 35, 255-269.

SZCZYGIEL, et al., "Intracytoplasmic sperm injection is more efficient than in vitro fertilization for generating mouse embryos from cryopreserved spermatozoa," (2002), Biology of Reproduction 67, 1278-1284.

SZTEIN, et al., "Comparison of permeating and nonpermeating cryoprotectants for mouse sperm cryopreservation," (2001), Cryobiology 42, 28-39.

THORNTON, et al., "Large numbers of mice established by in vitro fertilization with cryopreserved spermatozoa: Implications and applications for genetic resource banks, mutagenesis screens, and mouse backcrosses," (2006), Mammalian Genome 10, 987-992.

BYERS, et al., "Performance of ten inbred mouse strains following assisted reproductive technologies (ARTs)," (2006), Theriogenology 65(9): 1716-26.

SZTEIN, et al., "In vitro fertilization with cryopreserved inbred mouse sperm," (2000), Biol Reprod 63(6): 1774-80.

NAKAGATA, "Cryopreservation of mouse spermatozoa," (2000a), Mammalian Genome 11, 572-576.

NAKAGATA, "Mouse Spermatozoa Cryopreservation," (2000b), J Mamm Ova Res 17, 1-8.

NEILD D M, Brouwers J F, Colenbrander B, Aguero A, Gadella B M (2005). Lipid peroxide formation in relation to membrane stability of fresh and frozen thawed stallion spermatozoa. Mol Reprod Dev. 72(2):230-8.

GUTHRIE H D, Welch G R (2006). Determination of intracellular reactive oxygen species and high mitochondrial membrane potential in Percoll-treated viable boar sperm using fluorescence-activated flow cytometry. J Anim Sci. 84(8):2089-100.

The invention claimed is:

1. A kit for use in cryopreserving mammalian sperm, comprising a composition of at least three components for cryopreserving mammalian sperm, wherein the at least three components are: at least one cryoprotectant, at least one membrane protectant, and monothioglycerol, wherein the at least one cryoprotectant, at least one membrane protectant and monothioglycerol are provided in combination in a single receptacle; and instructions for use thereof to cryopreserve mammalian sperm in the composition and thereby produce a greater number of live bona offspring compared to mammalian sperm of the same type cryopreserved in the composition without monothioglycerol.

2. The kit of claim 1, wherein the at least one cryoprotectant is selected from the group consisting of raffinose, lactose, trehalose, melibiose, melezitose, mannotriose, stachyose, dextran, hydroxy-ethyl starch, sucrose, maltitol, lactitol, glycerol, polyethyleneglycol, DMSO, ethylene glycol, propylene glycol, polyvinyl pyrrolidone, polyethylene oxide, and combinations thereof.

3. The kit of claim 1, wherein the at least one membrane protectant is selected from the group consisting of: casein, albumin, keratin, collagen, atelocollagen, elastin, gelatin, peptones, fibrinogen, fibronectin, egg yolk or a component thereof, a soy protein, a wheat protein, a corn protein, milk, milk powder, skim milk or a component thereof, a milk protein or a component thereof, a hydrolysate of one of the foregoing, a lipid, a chemically synthesized lipid, a synthetic lipid, phosphatidylglycerol, phosphatidic acid, 1,1',2,2'-tetra-acyl-cardiolipin, phosphatidylcholine, phosphatidylserine, phosphatidylethanolamine, a polyoxyethylene based lipid, arachidonic, linoleic, linolenic, myristic, oleic, palmitic or stearic fatty acids, cholesterol, Pluronic F-68, polyvinylalcohol, and combinations thereof.

4. The kit of claim 1, further comprising at least one additional free radical scavenger.

5. The kit of claim 4, wherein the at least one free radical scavenger is a reducing agent selected from the group consisting of: beta-mercaptoethanol, dithiothreitol, tris(2-carboxyethyl)phosphine, dithioerythritol, thioredoxin, dithionite, 2-mercaptoethylamine, dimethyl thiourea, DMSO, nordihydroguaiaretic acid (NDGA), 2,3-dimercapto-1-propanol, hydroquinone, and combinations thereof.

6. The kit of claim 4, wherein the at least one free radical scavenger is an antioxidant.

7. The kit of claim 4, wherein the at least one free radical scavenger is selected from the group consisting of an amino acid, an amino acid derivative, a vitamin, a vitamin derivative, butylated hydroxyanisole, butylated hydroxytoluene, dihydrolipoic acid, tetrahydropapaveroline, 2-thiobarbituric acid, taurine, dimercaptosuccinic acid, allopurinol, deferoxamine, melatonin, catalase, glutathione peroxidase, superoxide dismutase, steroids, reduced glutathione, glutathionine, and combinations thereof.

8. The kit of claim 1, further comprising a container for the receptacle.

9. The kit of claim 8, wherein the container is a cryogenic vessel.

10. The kit of claim 9, wherein the cryogenic vessel is a styrofoam container or an insulated container.

11. The kit of claim 1, further comprising a receptacle for mammalian sperm.

12. The kit of claim 11, wherein the receptacle for mammalian sperm is selected from the group consisting of: a straw, a glass ampoule, a cryotube and a cryovial.

13. The kit of claim 11, further comprising a float for use in floating the receptacle for mammalian sperm on the surface of a cryogenic liquid disposed in the container.

14. The kit of claim 1, wherein the instructions are instructions to cryopreserve rodent sperm in the composition and thereby produce a greater number of live born offspring compared to rodent sperm of the same type cryopreserved in the composition without monothioglycerol.

15. The kit of claim 1, wherein the cryoprotectant is raffinose.

16. The kit of claim 1, wherein the membrane protectant is skim milk.

17. A kit for use in cryopreserving rodent sperm, comprising a composition for cryopreserving rodent sperm comprising raffinose, skim milk and monothioglycerol in a single receptacle; and instructions for use thereof to cryopreserve rodent sperm in the composition and thereby produce a greater number of live born offspring compared to rodent sperm of the same type cryopreserved in the composition without monothioglycerol.

* * * * *

UNITED STATES PATENT AND TRADEMARK OFFICE
CERTIFICATE OF CORRECTION

PATENT NO. : 8,685,637 B2
APPLICATION NO. : 13/723721
DATED : April 1, 2014
INVENTOR(S) : G. Charles Ostermeier et al.

Page 1 of 1

It is certified that error appears in the above-identified patent and that said Letters Patent is hereby corrected as shown below:

In the Claims

Column 37, claim 4, line 28, delete "additional."

Signed and Sealed this
Ninth Day of September, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,685,637 B2
APPLICATION NO. : 13/723721
DATED : April 1, 2014
INVENTOR(S) : G. Charles Ostermeier et al.

Page 1 of 1

It is certified that error appears in the above-identified patent and that said Letters Patent is hereby corrected as shown below:

In the claims
Column 37, line 3: Replace "bona" with --born--.

Signed and Sealed this
Thirty-first Day of May, 2016

Michelle K. Lee
*Director of the United States Patent and Trademark Office*